(12) United States Patent
Brushett

(10) Patent No.: US 12,121,206 B2
(45) Date of Patent: Oct. 22, 2024

(54) ACCURATE Z-OFFSET CALIBRATION FOR OCT SYSTEM

(71) Applicant: CANON U.S.A., INC., Melville, NY (US)

(72) Inventor: Christopher Douglas Brushett, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 449 days.

(21) Appl. No.: 17/679,834

(22) Filed: Feb. 24, 2022

(65) Prior Publication Data

US 2023/0263368 A1 Aug. 24, 2023

(51) Int. Cl.
- *A61B 1/00* (2006.01)
- *A61B 5/00* (2006.01)
- *G01B 9/02091* (2022.01)

(52) U.S. Cl.
CPC ...... *A61B 1/00057* (2013.01); *A61B 1/00165* (2013.01); *A61B 5/0066* (2013.01); *G01B 9/02091* (2013.01)

(58) Field of Classification Search
None
See application file for complete search history.

(56) References Cited

U.S. PATENT DOCUMENTS

| | | | |
|---|---|---|---|
| 7,813,609 B2 | 10/2010 | Petersen et al. | |
| 8,100,893 B2 | 1/2012 | Dadisman | |
| 8,116,605 B2 | 2/2012 | Petersen et al. | |
| 8,395,781 B2 | 3/2013 | Kemp et al. | |
| 9,301,687 B2 | 4/2016 | Kemp | |
| 9,596,993 B2 | 3/2017 | Kemp et al. | |
| 9,702,762 B2 | 6/2017 | Friedman et al. | |
| 10,206,585 B2 | 2/2019 | Kemp et al. | |
| 10,743,749 B2 | 8/2020 | Yamada | |
| 10,782,117 B2 | 9/2020 | Elmaanaoui | |
| 10,791,923 B2 | 10/2020 | Wu | |
| 11,147,453 B2 | 10/2021 | Yamada et al. | |
| 2009/0122320 A1 | 5/2009 | Petersen et al. | |
| 2013/0182259 A1 | 7/2013 | Brezinski et al. | |

(Continued)

FOREIGN PATENT DOCUMENTS

| JP | 2017-225599 A | 12/2017 |
|---|---|---|
| WO | 2008/044539 A1 | 4/2008 |

*Primary Examiner* — Raymond L Nimox
(74) *Attorney, Agent, or Firm* — Canon U.S.A., Inc., IP Division

(57) ABSTRACT

An optical coherence tomography (OCT) system comprises: an imaging catheter; a calibration phantom removably arranged at least partially surrounding the distal end of the catheter; and a processor configured to control the catheter to acquire OCT images. The phantom has known dimensions and specific optical properties which provide non-changing calibration fiducials that span the imaging range of the system. The phantom is imaged by the catheter upon first connection to the system. The processor calculates a thickness of the phantom in the OCT image, and preforms z-offset calibration by setting the position of a phantom surface in the OCT image to a known nominal value. The known nominal value is related to one or more of the known thickness of the phantom or a diameter of the catheter sheath or a nominal angle of the light beam or the imaging range of the system.

22 Claims, 10 Drawing Sheets

(56) References Cited

U.S. PATENT DOCUMENTS

| | | | |
|---|---|---|---|
| 2015/0168250 A1* | 6/2015 | Saxer | G01B 9/02064 |
| | | | 356/479 |
| 2019/0298174 A1* | 10/2019 | Watanabe | A61B 5/0066 |
| 2020/0355557 A1 | 11/2020 | Friedman et al. | |
| 2021/0190476 A1* | 6/2021 | Johansson | A61B 5/0066 |

\* cited by examiner

ACCURATE Z-OFFSET CALIBRATION FOR OCT SYSTEM

CROSS-REFERENCE TO RELATED APPLICATIONS n/a

BACKGROUND INFORMATION

Field of Disclosure

The present disclosure generally relates to medical devices. More particularly, the disclosure is directed to systems and methods for z-offset calibration of OCT catheters using a calibration phantom.

Description of Related Art

Optical Coherence Tomography (OCT) imaging uses interferometric techniques to acquire images of objects with micrometer (μm) resolution over depth ranges of several millimeters (mm). An important aspect of OCT imaging is the requirement that the optical path length of the sample arm and the reference arm must be matched to ensure the interference effect being recorded corresponds to a desired depth within the object. In medical applications, depending on the particular procedure, the object being imaged could be a biological target, such as the retina, the wall of an artery, the lining of the esophagus, or other bodily lumen of a patient.

In cardiovascular OCT, an imaging catheter, which can be several meters long, is introduced through the lumen of a vessel to image the vessel wall. The catheter irradiates the vessel wall with a beam of near infrared (NIR) light emitted radially from the catheter's distal end. The light penetrates into the vessel wall and is reflected back (back-scattered) by tissue layers of the vessel wall to be collected again at the distal end of the catheter. In order to acquire a 360 degree view of the vessel wall, the catheter uses an imaging core that is rotated by a fiber optic rotary joint (FORJ), and is simultaneously moved (translated) longitudinally during the rotation so that light is detected as a series of lines in the form of a helical pattern. The longitudinal movement of the imaging core is commonly performed by mechanically pulling the imaging core from the tip (distal end) back towards the proximal end of the catheter. Therefore this process is referred to as a "pullback" operation. A digital signal processor (DSP), such as computer processor, is used to digitize the series of helically scanned lines, and to form two dimensional (2D) or three dimensional (3D) OCT images, which are displayed on a screen.

One of the challenges in forming accurate OCT images is the difficulty in matching the optical path length (OPL) of the sample and reference arms. In OCT, by convention, the Cartesian 3D space defined by x-y-z vectors is represented in polar coordinates, where angle and radial distance are represented on the x-y plane and the lumen length is represented along the z-axis. In an imaging procedure, when the catheter is inserted into a bodily lumen, the outer surface of the catheter sheath is used as a reference point, and distances between the catheter and the vessel tissue are measured outward from this reference location. During image reconstruction, the scanned lines are treated as if they originate at the center of the catheter and the depth of imaging is measured using the catheter sheath as the reference point, but this is based on assumption that the path length of light through the catheter is invariable. However, when a catheter is inserted into the body of a patient, the delicate optics inside the catheter can be subject to stresses that can distort the optical path length. For example, due to changes in room temperature versus body temperature (between outside and inside of a patient's body) an optical fiber may stretch by as much as one millimeter during imaging. Naturally, this changes the reference point, such that if a diameter is measured on that image, the diameter will be wrong by as much as two millimeters. Similarly, an OCT system may require catheters of different dimensions during a single procedure. In this case too, the reference point would change depending on the catheter used.

To account for variations in catheter length between different catheter devices or to account for variations in the path length of a single catheter, a calibration step, referred to as "z-offset calibration", is performed to adjust the reference arm length to match the length of the sample arm (catheter and sample). To achieve this calibration step, current commercial OCT systems use calibration fiducials (e.g., radiopaque markers) built into the catheter sheath and adjust the optical path length of the reference arm such that reflections from the fiducials (e.g., the outer surface of the sheath) matches reflections from the reference arm to within a specified nominal dimension. Examples of z-offset calibration using fiducial reflections from the catheter sheath or from other reflective surfaces have been disclosed in several patents including, for example, U.S. Pat. No. 9,702,762 (Friedman), U.S. Pat. Nos. 9,596,993, 9,301,687 and 8,395,781 (Kemp), U.S. Pat. Nos. 7,813,609 and 8,116,605 (Petersen) and U.S. Pat. No. 11,147,453 (Yamada), all of which are incorporated by reference herein for all purposes.

The use of the catheter sheath for z-offset calibration has become the industry standard. While the use of reflective fiducials or layers of the catheter sheath provides a useful method to achieve z-offset calibration, this technique can still be subject to errors arising from the tolerance of the sheath outer diameter (OD), variable sheath appearance in the OCT image, non-uniform rotational distortion (NURD), non-concentricity of the sheath, variability in beam angle of the light emitted by the catheter, limitation in axial resolution of the OCT system, user error or algorithm error identifying an edge other than the intended fiducial in the OCT image, an combinations thereof. In other words, the use of reflective fiducials from any structure permanently built-in or affixed to the catheter body is inherently susceptible to measurement errors due to one or more of the reasons stated above.

Therefore, there remains a need for improved systems and methods for accurate z-offset calibration of OCT catheters.

SUMMARY OF EXEMPLARY EMBODIMENTS

The present disclosure provides improved systems and methods for accurate z-offset calibration of an OCT catheter by using a calibration phantom not affixed to the catheter body (i.e., provided separate from the catheter body) to perform room temperature calibration before the catheter is used in a patient. In addition, the present disclosure provides improved systems and methods for ongoing (continuous) calibration during an intraluminal imaging procedure. These novel system and methods address one or more sources of calibration error and thereby produce more accurate OCT images.

According to at least one embodiment of the present disclosure, an optical coherence tomography (OCT) system comprises a catheter body spanning from a proximal end to a distal end; a calibration phantom having a thickness and configured to be placed in optical alignment with an imaging window at the distal end of the catheter body; and a processor operatively connected to catheter body. The catheter body includes an imaging core configured to emit a light beam through the imaging window at a nominal angle with respect to the catheter body. The processor is configured to control the imaging probe to acquire an OCT image of the calibration phantom by irradiating the calibration phantom with the light beam, and collecting backscattered light from a surface of the calibration phantom. The processor is further configured to (a) determine a position of the surface of the calibration phantom in OCT image, and (b) preform z-offset calibration by setting the position of the surface of the calibration phantom in the OCT image to a known nominal value.

The processor is further configured to measure (i) a thickness of the calibration phantom in the OCT image, and (ii) calculate an angle of the light beam transmitted through the calibration phantom. When the calibration phantom is a cylindrical tube having an inner diameter (ID) and an outer diameter (OD), the processor measures the thickness of the calibration phantom in the OCT image as the difference between OD minus the ID. Then, the processor calculates the angle of the light beam transmitted through the calibration phantom based on the nominal beam angle modified by the phantom index of refraction and the phantom known thickness as compared to the measured thickness of the calibration phantom in the OCT image minus the effects of the system's axial resolution, according to the following formula Eq. (1):

$$\theta_{cath} = \arccos(L_{nom} * \cos(\theta_{nom})/(L_m - R_A)$$

Where $\theta_{nom}$ and $L_{nom}$ are the nominal beam angle for the phantom index and the known phantom thickness (specified values stored in the system), $R_A$ is the axial resolution of the system, and $L_m$ is the calculated thickness of the phantom in the OCT image. The expression "arccos" means the mathematical expression Arc Cosine which is the inverse cosine function of a given argument. Using the mean thickness of the phantom instead of any single surface like the catheter sheath removes any effect of NURD on the measurement which reduces one or more sources of calibration error. Subtracting the axial resolution from the measured thickness of the phantom accounts for the fact that the bright signal of the phantom in the OCT image will be blurred by half a resolution cell on either side.

The processor is configured to perform z-offset calibration by adjusting the OCT image to match the measured ID of the phantom to the nominal value like a standard OCT z-offset calibration but using the phantom ID instead of the sheath. In this manner, the catheter is calibrated for room temperature air.

After the catheter is calibrated for room temperature air, the user can introduce the catheter into a bodily lumen of a patient. Once the catheter enters the body of a patient, and scans the lumen through flushing media (angiographic contrast or saline), the catheter can be recalibrated but only for z-offset. The beam angle may change slightly by the known ratio of refractive indexes between the flushing media inside the lumen and the air temperature phantom calibration; this change can be accounted-for through the media setting in the system. Z-offset calibration inside the lumen can be done manually or automatically using standard z-calibration methods for calibrating to the sheath.

In at least some embodiments, the system can be configured for continuous z-offset calibration. In order to automate ongoing calibration after the catheter is removed from the phantom, the system is configured to target a new calibration fiducial in the catheter itself which will remain present during in vivo imaging. For the new calibration fiducial, any fiducials conventionally known in the art can be used. For example, catheter sheath OD can be used, but a more accurate calibration can be achieved by using the initial phantom calibration performed outside the patient's body to improve the fiducial calibration inside the body. This can be done using the catheter sheath by measuring the OD of the sheath while in the phantom after initial calibration and then adjusting the sheath to that value on subsequent images instead of using the nominal sheath diameter. This process removes a calibration error due the sheath diameter variability.

A more accurate continuous calibration can be achieved by using signature signals from surfaces within the lens or other component of the catheter structure. In this case, however, instead of using pre-selected surfaces with known real diameters or locations within the catheter, the system software can be configured (programmed) to effectively capture a snapshot of all the surfaces and signals within the lens as they actually appear while calibrated with the phantom, and then match the pattern of surfaces and signal to maintain continuous calibration in each OCT image frame. In this embodiment, initial calibration is done using the calibration phantom, as explained above, then the system is trained to key-in on signature signals from the lens or other reflective surface for subsequent calibration in vivo inside the patient's body. To achieve fully automated continuous calibration with no user input, the system can be configured to compare signals or a pattern of signals acquired in vivo to the signals acquired during initial calibration done the phantom.

While standard z-offset calibration involves setting some surface in the image to a known nominal value which adjusts for variation in optical length from catheter to catheter, the present disclosure proposes using two known surfaces in a phantom to add an extra degree of freedom, and calibrate to correct for variation not only in catheter length but also in catheter angle to get higher accuracy. And then the newly proposed method of continuous calibration carries the gains of two degrees of freedom calibration forward to in vivo imagining without the phantom.

These and other objects, features, and advantages of the present disclosure will become apparent upon reading the following detailed description of exemplary embodiments of the present disclosure, when taken in conjunction with the appended drawings, and provided claims.

DETAILED DESCRIPTION OF EXEMPLARY EMBODIMENTS

Figure 1:
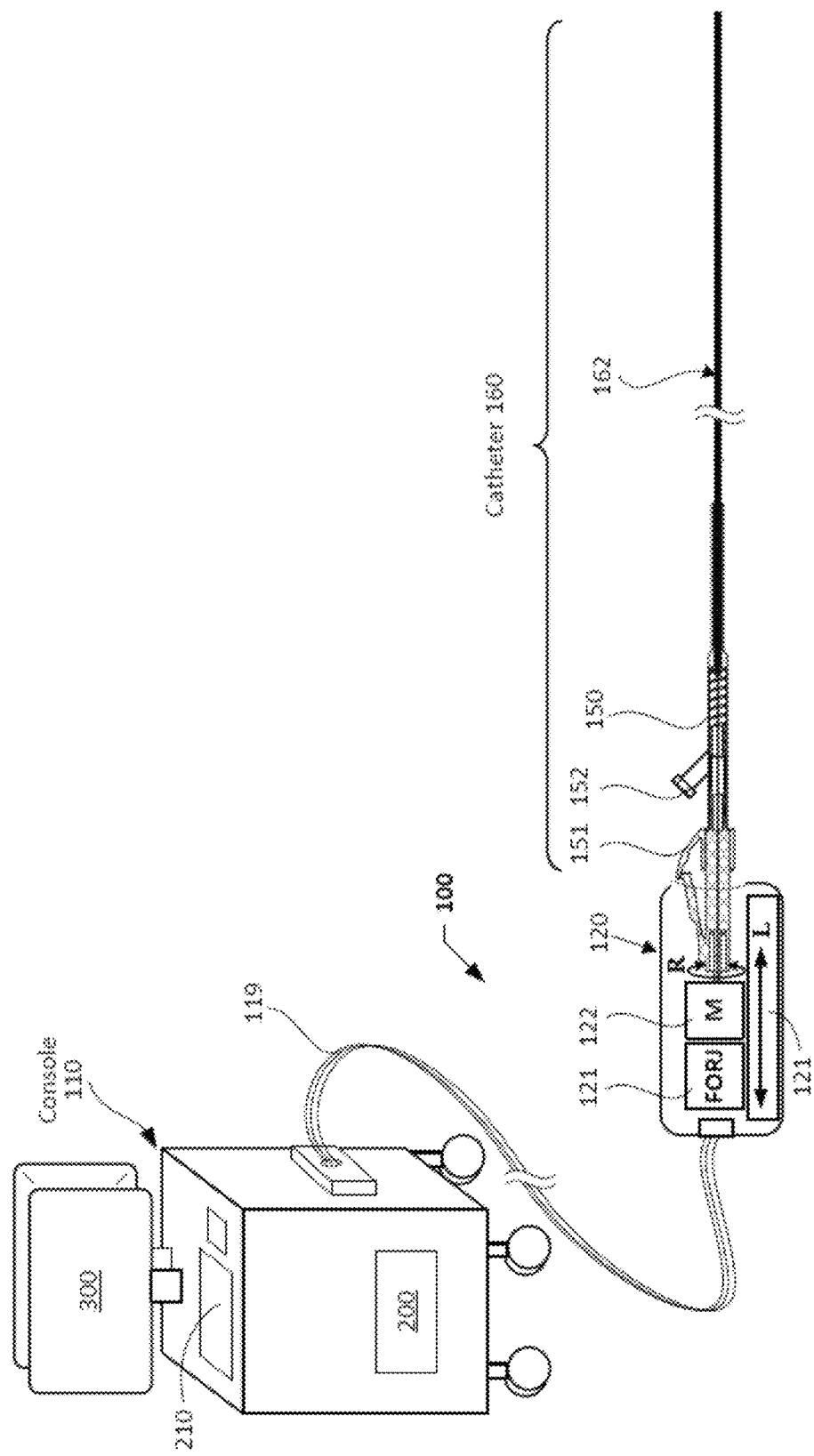
FIG. 1 is a diagram of an OCT system 100 with a catheter 160 requiring z-offset calibration, according to the present disclosure.

Before the various embodiments are described in further detail, it is to be understood that the present disclosure is not limited to any particular embodiment. It is also to be understood that the terminology used herein is for the purpose of describing exemplary embodiments only, and is not intended to be limiting.

Throughout the figures, the same reference numerals and characters, unless otherwise stated, are used to denote like features, elements, components or portions of the illustrated embodiments. In addition, while the subject disclosure is described in detail with reference to the enclosed figures, it is done so in connection with illustrative exemplary embodiments. It is intended that changes and modifications can be made to the described exemplary embodiments without departing from the true scope of the subject disclosure as defined by the appended claims. Although the drawings represent some possible configurations and approaches, the drawings are not necessarily to scale and certain features may be exaggerated, removed, or partially sectioned to better illustrate and explain certain aspects of the present disclosure. The descriptions set forth herein are not intended to be exhaustive or otherwise limit or restrict the claims to the precise forms and configurations shown in the drawings and disclosed in the following detailed description.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without limitation and without departing from structural or functional meaning.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated. Further, in the present disclosure, the transitional phrase "consisting of" excludes any element, step, or component not specified in the claim. It is further noted that some claims or some features of a claim may be drafted to exclude any optional element; such claims may use exclusive terminology as "solely," "only" and the like in connection with the recitation of claim elements, or it may use of a "negative" limitation.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to be inclusive of end values and includes all sub-ranges subsumed therein, unless specifically stated otherwise. As used herein, the term "substantially" is meant to allow for deviations from the descriptor that do not negatively affect the intended purpose. For example, deviations that are from limitations in measurements, differences within manufacture tolerance, or variations of less than 5% can be considered within the scope of substantially the same. The specified descriptor can be an absolute value (e.g. substantially spherical, substantially perpendicular, substantially concentric, etc.) or a relative term (e.g. substantially similar, substantially the same, etc.).

Unless specifically stated otherwise, as apparent from the following disclosure, it is understood that, throughout the disclosure, discussions using terms such as "processing," "computing," "calculating," "determining," "displaying," or the like, refer to the action and processes of a computer system, or similar electronic computing device, or data processing device that manipulates and transforms data represented as physical (electronic) quantities within the computer system's registers and memories into other data similarly represented as physical quantities within the computer system memories or registers or other such information storage, transmission or display devices. Computer or electronic operations described in the specification or recited in the appended claims may generally be performed in any order, unless context dictates otherwise. Also, although various operational flow diagrams are presented in a sequence(s), it should be understood that the various operations may be performed in other orders than those which are illustrated or claimed, or operations may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "in response to", "related to," "based on", or other like past-tense adjectives are generally not intended to exclude such variants, unless context dictates otherwise.

The present disclosure generally relates to medical devices, and it exemplifies embodiments of an optical probe which may be applicable to a spectroscopic apparatus (e.g., an endoscope), an optical coherence tomographic (OCT) apparatus, or a combination of such apparatuses (e.g., a multi-modality optical probe). The embodiments of the optical probe and portions thereof are described in terms of their state in a three-dimensional space. As used herein, the term "position" refers to the location of an object or a portion of an object in a three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of object in at least one degree of rotational freedom (up to six total degrees of freedom); the term "shape" refers to a set of posture, positions, and/or orientations measured along the elongated body of the object.

As it is known in the field of medical devices, the terms "proximal" and "distal" are used with reference to the manipulation of an end of an instrument extending from the user to a surgical or diagnostic site. In this regard, the term "proximal" refers to the portion (e.g., a handle) of the instrument closer to the user, and the term "distal" refers to the portion (tip) of the instrument further away from the user and closer to a surgical or diagnostic site. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

As used herein the term "catheter" generally refers to a flexible and thin tubular instrument made of medical grade material designed to be inserted through a narrow opening into a bodily lumen (e.g., a vessel) to perform a broad range of medical functions. The more specific term "optical catheter" refers to a medical instrument comprising an elongated bundle of one or more flexible light conducting fibers disposed inside a protective sheath made of medical grade material and having an optical imaging function. A particular example of an optical catheter is fiber optic catheter which comprises a sheath, a coil, a protector and an optical probe. In some applications a catheter may include a "guide catheter" which functions similarly to a sheath.

In the present disclosure, the terms "optical fiber", "fiber optic", or simply "fiber" refers to an elongated, flexible, light conducting conduit capable of conducting light from one end to another end due to the effect known as total internal reflection. The terms "light guiding component" or "waveguide" may also refer to, or may have the functionality of, an optical fiber. The term "fiber" may refer to one or more light conducting fibers. An optical fiber has a generally transparent, homogenous core, through which the light is guided, and the core is surrounded by a homogenous cladding. The refraction index of the core is larger than the refraction index of the cladding. Depending on design choice some fibers can have multiple claddings surrounding the core.

[Note to reviewer: start detailed review here]

According to one aspect of the present disclosure, an automatic z-offset calibration procedure is proposed to produce correct OCT images. In order to achieve a more accurate calibration, a phantom with specified optical properties is used to provide reliable calibration fiducials which span the imaging range of the OCT system. In one embodiment, a phantom having a circular cross-section with accurate inner diameter (ID) and outer diameter (OD), and a known index of refraction is built into the catheter packaging. The phantom is imaged upon first connection of the catheter to the OCT system. Then, the system performs z-offset calibration with respect to characteristic parameters (known thickness and index of refraction) of the phantom. Here, imaging the phantom and initial z-offset calibration can be done even before removing the catheter from its protective packaging hoop. Instead of calibrating with one degree of freedom to one fiducial (the sheath OD) as is conventionally done, the system according to the present disclosure can calibrate with two degrees of freedom (z-offset and beam angle) to two stable fiducials provided by the ID and OD of the phantom. This innovation can minimize the risks of measurement error, can make calibration easier to automate, can suppress or reduce one or more sources of calibration error (e.g., reduce the angle error), thereby resulting in an improvement in calibration accuracy at all diameters.

<OCT System>

FIG. 1 illustrates an example embodiment of an OCT system 100 with a catheter 160 requiring z-offset calibration according to the present disclosure. The OCT system 100 includes a system console 110, a patient interface unit (PIU) 120, and a catheter 160. The system console 110 is configured (programmed) for controlling operations of the system as a whole, and for processing OCT image data acquired by the system using the catheter 160. The system and methods disclosed here employ an OCT system having a conventional interferometer, such as a Michelson interferometer, where the OPL of the sample arm and the OPL of the reference arm are matched to have substantially equal optical path lengths. The OCT system 100 can be implemented according to a variety of known OCT principles, including time-domain optical coherence tomography (TD-OCT) or frequency-domain optical coherence tomography (FD-OCT). FD-OCT may include spectral domain OCT (SD-OCT) or swept source OCT (SS-OCT).

Briefly, in OCT system 100, light from a light source (not shown) is directed onto a beam splitter (e.g., 50/50 splitter), and divided into two light beams. One of the beams is incident onto the sample to be imaged, while the second beam travels a reference path with a variable path length and time delay. The variable path length and time delay can be achieved by a variable optical delay line (VDL) implemented by a motorized optical delay line (MDL) or by a fiber-based Optic Delay Lines (ODL) as disclosed, for example, in U.S. patent Ser. No. 10/782,117 which is incorporated by reference herein for all purposes. The backscattered light from the sample is interfered with reflected light from the reference arm and detected with a photodetector at the output of the interferometer. If the light source is coherent (e.g., a continuous wave laser), then interference fringes will be observed as the relative path lengths are varied. If the light source has low-coherence or emits short pulses of light, the interference of the light reflected from the sample and reference arms can occur only when the two optical path lengths match to within the coherence length of the light source. The echo time delay and intensity of backscattered light from sites within the sample can be measured by detecting and demodulating the interference output of the interferometer while scanning the reference path length.

Figure 3A:
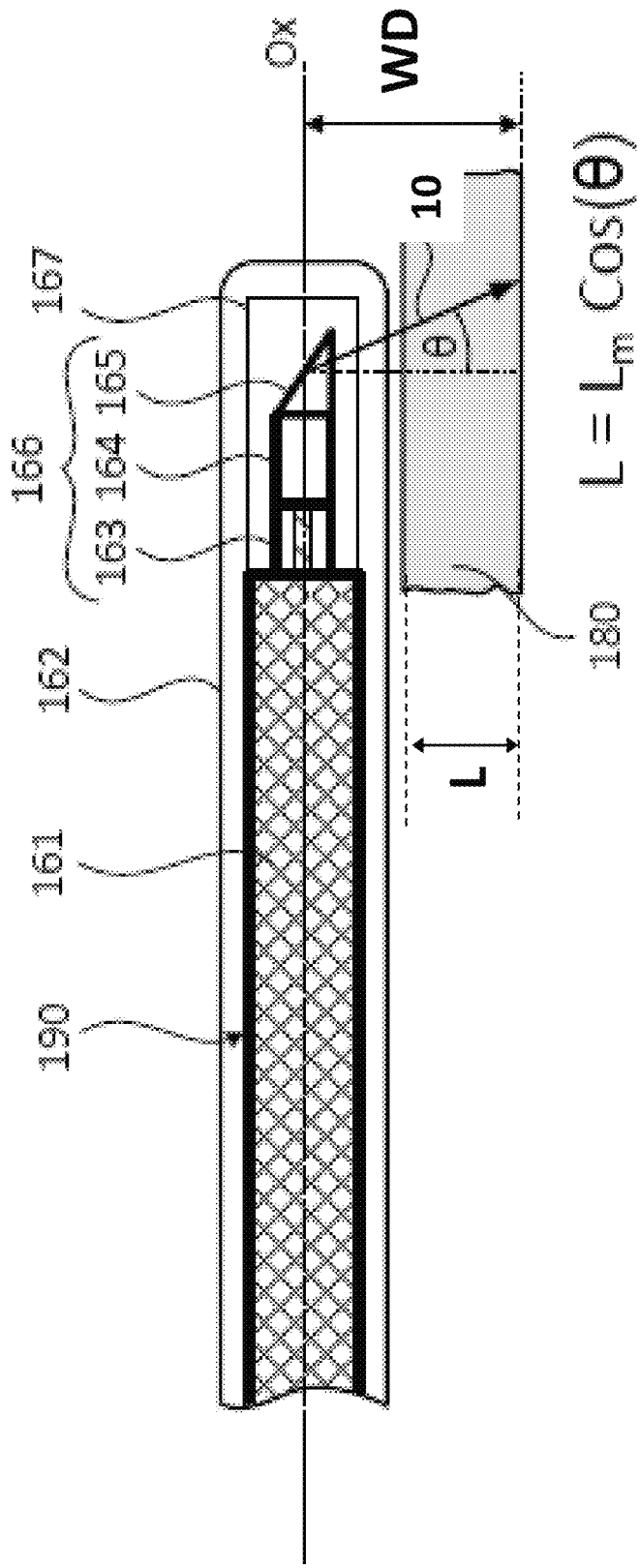
FIG. 3A illustrates an exemplary representation of a distal end of catheter 160 positioned such that distal optics 166 of the imaging core are optically aligned with the calibration phantom 180, according to an embodiment of the present disclosure.

The catheter 160 generally comprises a catheter handle 150 and a flexible sheath 162 (catheter body or tubular body) configured to be inserted into a bodily lumen of a patient. The catheter handle 150 connects to the PIU 120 via a catheter connector 151. The sheath 162 encloses an imaging core 190 which includes a torque coil 161, an optical fiber 163, a distal optics assembly 166, and a can 167 (as illustrated in FIG. 3A). In at least some embodiments, the catheter 160 may also include one or more than one access port 152 for, for example, injecting contrast agent (flushing media) for blood clearance purposes.

The PIU 120 connects the catheter 160 to the console 110 using a cable bundle 119. The system console 110 includes, among other things, a computer 200, a user interface 210, and one or more displays 300. The system console 110 may also include other mechanical, electronic and/or optical components, such as a light source, optical fibers, one or more optical sensors, an optical delay line, etc., necessary for catheter-based OCT imaging. An example of light source is a laser source (swept source); and an example of an optical sensor is a photodiode. The computer 200 may include a central processing unit (CPU) comprising one or more processors (e.g., a microprocessor, microcontroller, digital signal processor, or the like) along with computer program logic. In an exemplary imaging procedure, the computer 200 controls the imaging core 190 via the PIU 120 to obtain OCT images of a biological lumen, such as a cardiovascular vessel of a patient.

The PIU 120 is the main interface between the catheter 160 and the system console 110. The system console 110 and PIU 120 are connected to each other by the cable bundle 119. The cable bundle 119 comprises cables for transmitting electrical power to the PIU and for electronic signaling between the PIU and the console. The cable bundle 119 also includes optical fibers for transmitting light to/from the catheter 160. The PIU 120 may provide a user interface, such as actionable buttons or switches (not shown), for controlling the imaging functions of the catheter from the sterile field. The PIU 120 is comprised of a beam combiner (not shown), a fiber optic rotary joint (FORJ) 121, and a pullback unit including a rotational motor (M) 122 and a linear stage (L) 121. The PIU 120 together with its internal components is a multi-use unsterile component. On the other hand, the catheter 160 and its handle 150 are intended to be sterile components configured for single-use or limited-use operations. Therefore, during use of the OCT system 100, the entire PIU 120 is covered with a sterile drape or bag (not shown), and the proximal end of the catheter 160 is manually connected to PIU 120 by a user maneuvering the catheter handle 150 and/or the catheter connector 151. When the user attaches the catheter 160 to the PIU 120, the system performs a calibration process.

<Calibration Phantoms>

Figure 2:
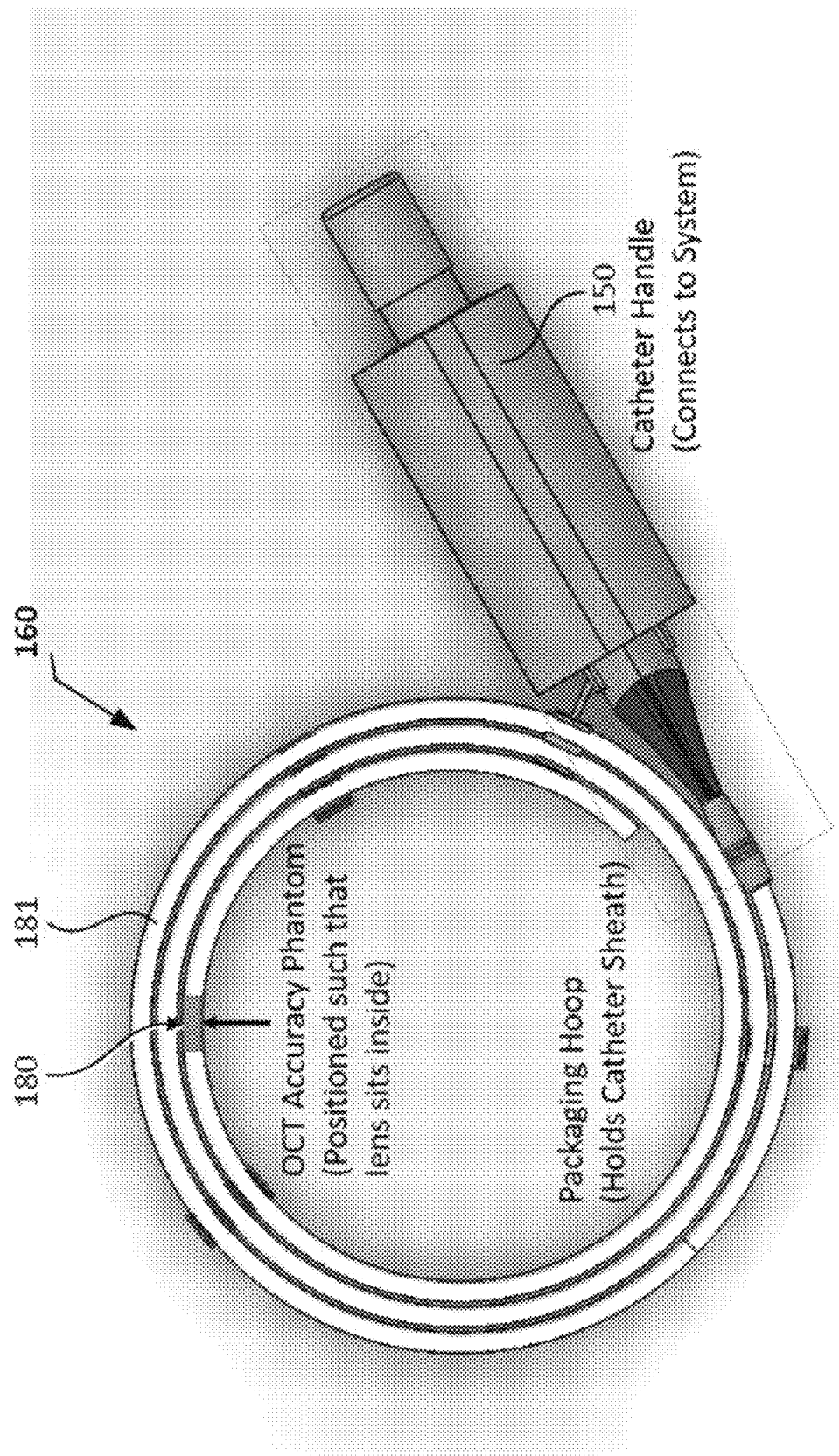
FIG. 2 shows an example of the catheter 160 comprising a catheter handle 150 and a calibration phantom 180, according to an embodiment of the present disclosure.

FIG. 2 shows an example of the catheter 160 comprising a catheter handle 150 and a calibration phantom 180. For medical use, catheter 160 and its handle 150 are generally provided in a sterile packaging such as a box, pouch, tray, die-card, etc. The outer sheath of the catheter is enclosed in a disposable hoop 181. According to one or more embodiments of the present disclosure, the phantom 180 is constructed out of glass or glass-like material or a transparent polymer with precise dimensions and a known and homogeneous index of refraction. The phantom 180 is designed with an inner diameter (ID) and outer diameter (OD) spanning a short length sufficient to cover a pullback distance of the OCT system. The phantom ID is close to the outer diameter (OD) of the catheter sheath, and the phantom OD is near the maximum imaging range (focusing distance) of the OCT system. For example, for a typical OCT catheter with a sheath OD of 0.8 millimeters (mm) that is used in vessels of up to 5 mm in diameter, the calibration phantom 180 may have an ID of approximately 1.0 mm and an OD of approximately 5.0 mm. That is, according to at least one embodiment of the present disclosure, the calibration phantom 180 may have an ID approximately equal to or about 10-20% greater than the OD of the catheter sheath, and can have an OD approximately equal to or greater than the ID of the bodily lumen to be imaged. Also, said in another way, the phantom 180 may have a thickness substantially equal to the imaging range of the OCT system.

Here, a "maximum range" of the OCT imaging system as it relates to the phantom OD can be considered under a few different ways. OCT systems have a Field-of-View (FOV) which determines the maximum object size that can be viewed on the display of the system. The FOV is a design choice for the catheter with tradeoffs to resolution. For coronary OCT catheters, for example, the FOV is usually set around 7 to 10 mm, so one option would be to have the calibration phantom OD near the FOV limit. There are also usually specific indications for use of an OCT system. Commercial coronary OCT systems are indicated for vessels in a range of 1.5 to 5.0 mm diameter. Therefore, the OCT system resolution should be tailored to similar ranges, and the phantom OD should be designed based on these parameters. This would usually be based on which range the accuracy of calibration needs to be proven during design verification. Another way to consider a "maximum range" is to think about actual clinical limits. Coronary vessels generally are between 2-4 mm with the left main sometimes going up as high as 6 mm. One of ordinary skill in the art would not expect to see vessels above 6 mm anywhere in the coronaries so the expected highest dimension of the vessel diameter could also be used as a reference for the OD phantom size. Therefore, a calibration phantom 180 can be specifically designed for each new catheter based on the catheter's design and application. In at least some embodiments, a calibration phantom 180 can be designed to fit different types of catheters taking into consideration the maximum range of the OCT system or the minimum/maximum size of the biological lumen to be imaged.

The material to fabricate the phantom 180 can be chosen such that the phantom 180 appears particularly brighter than other signals under OCT imaging. To that end, the phantom material may include glass doped with scattering agents such as Titanium oxide (TiO2) or Barium sulfate (BaSo4). In some embodiments, the phantom material may include well known polymers such as FEP, PET, PTFE, nylon and/or combinations thereof with or without doping (undoped). FEP (fluorinated ethylene propylene), PTFE (polytetrafluoroethylene: a synthetic fluoropolymer of tetrafluoroethylene) and FEP (polyethylene terephthalate) are similar in their material properties, and are widely used in medical devices due to their biomedical compatible properties. The phantom 180 can be built into the catheter packaging hoop 181 as shown in FIG. 2. Alternatively, the phantom 180 could be provided as a separate item elsewhere in the package of the catheter. Further alternatively, the phantom 180 can be permanently installed on/with the OCT system (e.g., attached to the console 110 or PIU 120), and configured to receive in its ID the catheter sheath distal end with or without the packaging hoop 181. In at least one embodiment, the diameter of the calibration phantom 180 can be adjustable so that the phantom can be used with catheters of different sizes. When the phantom 180 is provided as a separate component installed in the OCT system, a user would be required to manually place the catheter lens to be aligned with the phantom 180 prior to start a calibration routine. When the phantom 180 is provided as part of the sterile hoop 181, the phantom can be already in optical alignment with the imaging window of the catheter, so that room temperature calibration can be done before the catheter is removed from the sterile hoop 181.

In at least one embodiment, the calibration phantom 180 can be similar to a housing structure described by Dadisman in U.S. Pat. No. 8,100,893 which in incorporated herein by reference. Dadisman discloses a housing fixture built into the catheter packaging with physical dimensions to use as a calibration aide. According to Dadisman, the user manually uses the housing to hold the catheter lens a fixed distance from a detector in order to calibrate the power of a laser source. The OCT system of the present disclosure could use a similar housing structure to hold the lens of the catheter's imaging core in optical alignment with the housing such that the surfaces of the housing can be imaged and measured. The system can then calibrate the z-offset based on that measurement. However, to achieve the precision needed for improved OCT imaging, distance and thickness measurements are performed according to novel techniques disclosed herein. More specifically, the present disclosure uses a cylindrical phantom with a controlled wall thickness instead of a housing fixture as disclosed by Dadisman.

Cylindrical phantoms can be extruded or machined with very precise dimensions, such that the wall thickness measurement can be used to compensate for NURD. A calibration phantom can be doped with materials configured to enhance scattering and/or fluorescence effects to more easily and precisely detect the thickness of the phantom wall. Further the phantom of the present disclosure can be easily built into the protective hoop 181 at the lens starting position such that no additional steps are needed to perform the initial calibration. To minimize manufacturing costs, in at least some embodiments, the phantom 180 can be modified to have only part of its cylindrical body (e.g., an arc of about 45 to 180 degrees) made of glass or polymer doped with scattering and/or fluorescent agents. Alternatively, the hoop 181 can include a semi-cylindrical window made of glass or polymer doped with such scattering/fluorescent agents, as the calibration phantom 180. As long as the catheter can scan the inner and outer surfaces of the phantom 180, and the system can use the backscattered signal to effectively measure the wall thickness of the phantom, the shape of the phantom is not limited to cylindrical. Certainly other shapes like cones would work too; anything that is circular in cross section. The circularity is important for the basic z-offset step, so for the new phantom, in the cross section used, it is necessary at least one circular reference and a wall thickness.

<Initial Calibration with Calibration Phantom and Manual Correction>

In one embodiment, for initial calibration, at least part of the catheter 160 (e.g., handle 150) is removed from any external packaging such as a box, pouch, tray, die-card, etc., and connected to the PIU 120, while the catheter tip still remains in the protective hoop 181. If the phantom 180 is provided already mounted on or integrated into the protective hoop 181, as illustrated in FIG. 2, the imaging core can be controlled such that the catheter lens 164 is positioned inside the phantom 180 at the post connection start position. Then, when the OCT system completes the connection sequence to catheter, the computer 200 may automatically control the PIU 120 to immediately begin imaging and perform an automatic calibration process such that the optical path length of the sample arm matches the optical path length of the reference arm. In this manner, the initial z-calibration process can be performed even before the catheter has been removed from its sterile packaging hoop 181.

FIG. 3A illustrates an exemplary representation of a distal end of catheter 160 positioned such that one or more components of distal optics assembly 166 is aligned with the calibration phantom 180. As illustrated in FIG. 3A, the catheter 160 comprises the sheath 162 (outer sheath), which encloses the imaging core 190. The catheter 160 is connected at the proximal end thereof to the PIU 120 via the catheter handle 150 and the connector 151 (as shown in FIG. 1). The computer 200 controls the imaging core 190 to emit a light beam 10 from the distal end of the catheter at an angle with respect to the catheter axis. The imaging core 190 includes a torque coil 161, a distal optics assembly 166, and a can 167. The can 167 may include a transparent inner sheath or a metal can with a transparent window. The distal optics assembly 166 includes a distal end of the optical fiber 163 (e.g., a double clad fiber (DCF)), a lens 164 (e.g., a GRIN lens or a ball lens), and a beam directing component 165 (e.g., a reflecting or diffracting surface such as a mirror or a grating, respectively). Fabrication of the distal optics assembly 166 can be carried out with specialized splicing, cleaving and/or etching techniques to satisfy the mechanical strength and stability of the imaging core. See, for example, U.S. patent Ser. No. 10/791,923 owned by the assignee of the present application; the disclosure of which is incorporated by reference.

Prior to initiating an imaging operation on a patient, the catheter handle 150 is grasped by a user and mechanically connected to the PIU 120 so that a connector 151 a source of torque. Specifically, the catheter handle connection occurs when a user manually grabs the catheter handle 150 and connects the proximal end (connector 151) of a new catheter 160 to the PIU 120. Once the catheter is connected to the PIU 120, the connection is detected by the console 110 with a sensor such as a touch sensor, an optical sensor, magnetic sensor, and/or a pressure sensor (not shown). The mechanical connection detected by a sensor (not shown) is converted to an electrical signal, and the electrical signal is transmitted to the console 110 (e.g., through the cable bundle 119). The system recognizes the catheter handle connection by executing software instructions with the CPU of computer 200. An example of a process for detecting the attachment of a new catheter to the PIU is described in applicant's published U.S. patent Ser. No. 10/743,749, which is incorporated by reference herein for all purposes. After the computer 200 has determined that the catheter 160 is connected (inserted) to the PIU 120, the computer 200 controls the pullback unit 121 to ensure that the lens 164 or other reflective component is optically aligned with the phantom 180. To that end, for example, the computer 200 controls the linear stage 121 to move the imaging core 190 until the lens is arranged aligned with phantom 180, and an image of the phantom is observed in the display 300. Additionally or alternatively, the system controls the MDL in the reference arm to adjust the OPL of the reference arm until an appropriate OCT signal (an interference signal) of light reflected or backscattered by the phantom is acquired by the catheter.

The process of attaching the catheter and aligning the lens with the phantom may also be done manually by the user. In one embodiment, first a coarse calibration step is performed by the system to get the lens 164 in the imaging range of the phantom 180, and the remaining calibration (z-offset calibration) can be done manually by the user in an iterative manner. The presence of the phantom 180 makes the calibration process easier by avoiding or minimizing errors that occur when using only signature reflections from the catheter sheath as a fiducial.

OCT errors caused when using reflections from the sheath of the catheter can be broken down into 3 categories for this context, as follows:

1) Calibration Error: this is an error arising from the z-offset calibration feature itself. This is an offset error which is driven by the tolerance of the sheath dimension used for calibration, non-concentricity of the sheath, or distortion of the sheath caused by vibrations or NURD which cause the sheath to be or to appear of a different size and shape than expected. This error is mostly unavoidable because the sheath, even when using doped fiducials, is a fixed part of the imaging probe. Specifically any error arising from tolerance or non-concentricity of the sheath (or other reference surface such as a dedicated reflector attached to the sheath) is unavoidable, but error from distortions like NURD may be avoidable or correctable. The calibration disclosed herein provides two degrees of freedom by using the thickness of the phantom and the angle of the beam transmitted through the phantom mitigate NURD error, for example.

2) Measurement Error: this error is also an offset error arising from a user or algorithm performing the measurement. This error is driven largely by the axial resolution of the system which blurs features in the image, or may arise if the wrong calibration fiducial is identified for calibration. For example, a measurement error occurs when calibrating to the inner surface of the sheath when it is intended to calibrate to the outer surface. Friedman, Kent or Petersen mentioned above have proposed certain techniques to address this type of error. The present application improves on these conventional techniques by using the calibration phantom with 2 or more fiducials to account for both variation in optical length and variation in beam angle. This gives the OCT calibration an extra degree of freedom.

3) Angle Error: the angle error is a scaling error driven primarily by variations in the catheter beam angle. This can become a dominant error source for large diameter measurements and is not addressed at all by conventional z-offset calibration techniques. Moreover, when other errors (calibration error or measurement error or NURD) are not properly addressed, the Angle Error is compounded and becomes more difficult to correct. In this case, after calibrating in phantom, the system uses new fiducial from catheter structure as stand-in for the phantom (can be the sheath OD which is commonly used for calibration but now rather than using the nominal OD of the catheter the system will use the actual measured OD in the calibrated state) and use that fiducial for ongoing calibration throughout procedure.

In FIG. 3A, to obviate one or more of the most common errors (calibration, measurement, and/or angle error), the specific dimensions of the phantom 180 are known a priori, and the optical path length through the phantom is accurately measured from the OCT image. Since the phantom is a component independent from the catheter sheath, the system can use the parameters of the calibration phantom to correct the errors arising from the catheter components caused by, for example, catheter ovalization, NURD, z-offset, inaccurate sample arm optical path measurement, and/or variation of beam angle.

More specifically, by referring back to FIG. 3A, it is considered that without the calibration phantom 180, a light beam 10 can scan the surface of an object located at a working distance (WD). When a phantom 180 having a known thickness L is placed to be surrounding the catheter sheath 162, the light beam 10 travels through the phantom a distance $L_m$. The distance traveled by beam 10 in the phantom is given by $L_m = t_m*[c/n]$, where $t_m$ is measured time, c is the speed of light, and n is the index of refraction of the phantom. However, when considering the beam angle, the actual thickness of the phantom 180 is given $L = L_m * Cos(\theta)$. To reconstruct an image of an object located at the working distance WD, the system must take into account not only the angle and distance traveled by the light beam 10, but also the system's axial resolution.

In this case, for a beam of light emitted at an angle theta ($\theta$) of about 19 to 25 degrees, an object is blurred due to one or more of the errors shown in Table 1, and/or due to limitations in the axial resolution of the system. These error sources don't all cause blurring, but axial resolution in particular causes blurring and that can be one error source by obscuring the exact edge point. If the sheath OD or the beam angle is off, such error will just shift the image such that measurements are a bit off, but not necessarily blurry. In contrast, axial resolution causes a measurement error by blurring the exact location of edge point.

TABLE 1

Example of error sources in conventional OCT imaging:

| Measurement Error | Calibration Error | Angle Error |
|---|---|---|
| Axial resolution = 0.02 mm | Sheath OD = 0.76-0.80 mm | Cos(19) = 0.946 |
| ±2% Error @ 1 mm | ±2% Error @ 1 mm | Cos(25) = 0.906 |
| ±0.4% Error @ 5 mm | ±0.4% Error @ 5 mm | ±2.1% Error @ 1 mm |
|  |  | ±2.1% Error @ 5 mm |

Axial resolution is related to parameters of the OCT light source, such as coherence length and bandwidth of the laser. There is a tradeoff between axial resolution and field-of-view (FOV) as it relates to the blurring on an image. Axial resolution is essentially a measurement of how wide a point source would appear in an image. So if axial resolution is 20 microns, then a point source will actually appear as a circle with a 20 micron diameter. When making measurements on a blurry image, users will disagree about where to place a measurement line within that 20 micron circle, and this can lead to measurement errors of up to 20 microns.

For the beam angle, the system must assume that the catheter is at the nominal beam angle when making measurements. Every measurement the system makes gets transformed to account for this beam angle by multiplying by cosine of the nominal angle. But if the actual beam angle of the device varies during imaging, this will introduce a scaling error on every measurement.

To avoid one or more of these errors, the beam angle of the light emitted from the catheter and transmitted through the phantom 180 is calculated with the following equation (1):

$$\theta_{cath} = \arccos(L_{nom} * Cos(\theta_{nom})/(L_m - R_A))$$ Eq. (1)

Where $\theta_{nom}$ and $L_{nom}$ are respectively the nominal beam angle and the nominal phantom thickness, $R_A$ is the axial resolution of the system, and $L_m$ is the measured thickness of the phantom. The nominal beam angle $\theta_{nom}$ for the phantom index and the nominal phantom thickness $L_{nom}$ can be specified values known from the manufacturer and stored in the system's memory.

The catheter has an angled mirror at the tip which reflects light outward and sets the beam angle. The actual physical angle of this mirror corresponds to the nominal beam angle ($\theta_{nom}$) if the beam were transmitted in air. When the beam hits another media like water, flushing media or blood inside the vessel, or the phantom material (polymer or glass), the beam angle changes based on the index of refraction and Snell's Law (n1/n2=sin α2/sin α1). There is a specification for the physical mirror angle and the nominal value of that beam angle is provided as a parameter in the OCT software. The OCT system may also factor the refractive index of the media being imaged as a parameter. If we know the refractive index of the phantom and set the OCT system to that index, the system will then know what the nominal beam angle should be in that phantom. If we happen to have a catheter that has a mirror right at the nominal angle for that phantom, then everything will already be accurate in terms of beam angle. But if the beam angle of the catheter differs from the nominal angle, then when the system goes to measure something like the thickness of the phantom, the system will get the thickness wrong by a ratio of the angles (i.e., nominal angle vs. measured angle). In Eq. (1), the term $L_{nom}$ is the known actual thickness of the phantom which the system will compare to the measured thickness in the image to see if there is an angle error or not. Therefore, the system calculates the catheter angle $\theta_{cath}$ to factor out any possible error of the beam angle. It is noted that, the OPL adjustment does not use or affect the thickness of the phantom. Rather, the thickness of the phantom tells us something about the angle of the catheter ($\theta_{cath}$) which basically sets the size of a pixel in the image. The OPL is then adjusted to match a single surface to its known position. If the beam angle and media are set (calibrated) correctly for the first surface, then the 2nd surface of the phantom should be in the right place too.

Figure 4B:
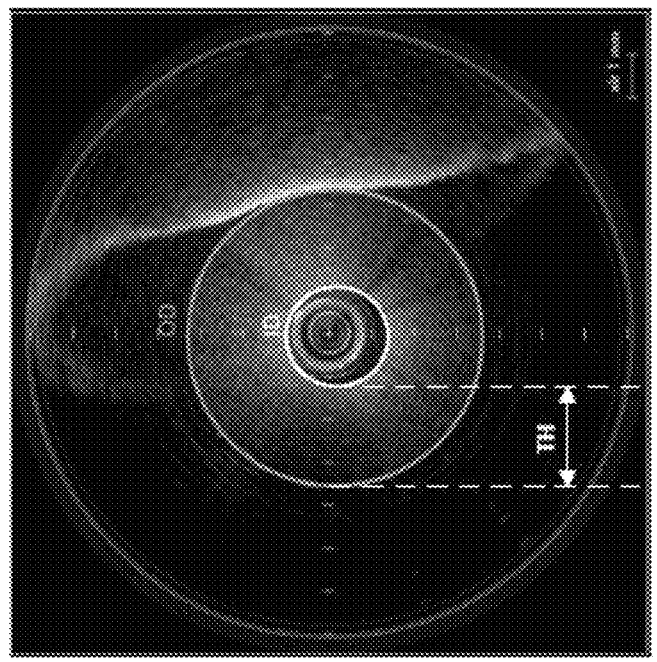
FIG. 4B shows an example of how the system accurately measures a thickness (TH) of the calibration phantom 180.
Figure 4A:
FIG. 4A shows an example image of a calibration phantom acquired after coarse calibration.

FIG. 4A shows an example image of a nylon phantom acquired after coarse calibration. With the phantom image shown on the screen display 300, the system next detects the ID and the OD of the phantom. Then, the system accurately measures the apparent thickness (TH) of the phantom in the image as the distance between the OD and ID. To improve accuracy, the system can measure the phantom thickness (TH) as the difference between the mean OD minus the mean ID by averaging several frames of the OCT image. FIG. 4B shows an OCT image of the calibration phantom 180 where several frames of the OCT image are averaged to more clearly show the reflections of ID and the OD, thereby allowing a more accurate measurement of the phantom thickness TH. The system can also be configured to calculate an average of the mean OD and the mean ID to be used as a reference for calibration. Then, the system can use the mean OD, the mean ID, and/or the average thereof as three separate fiducials increase calibration accuracy.

Using the thickness of the phantom (i.e., using two surfaces) instead of any single surface like the surface of the catheter sheath removes the effects of NURD on the measurement which reduces or eliminates at least one source of calibration error. In addition, subtracting the axial resolution from the measured thickness of the phantom accounts for the fact that the bright signal of the phantom will be blurred by half a resolution cell on either side of the image.

More specifically, a surface of the phantom acts as a point source in OCT imaging. Therefore, an image of the phantom is formed by detecting light reflected from the phantom surface and arranging points images in a circle while the catheter scans the phantom. But in the image of the phantom, a circle with diameter equal to the axial resolution is laid down at each point along the edge resulting in a thick line all the way around the image of the phantom. The actual edge of the phantom is at the center of this thick line which extends half a resolution cell to either side. But a user reading the image will perceive the phantom edge at the outer edge of the thick line which is off by half a resolution cell. This will overstate the OD and understate the ID each by a resolution cell, and will also overstate the thickness of the phantom by one cell. In system where accuracy is required to be 0.1 mm or better, the OCT image may include an error due to axial resolution.

Figure 4D:
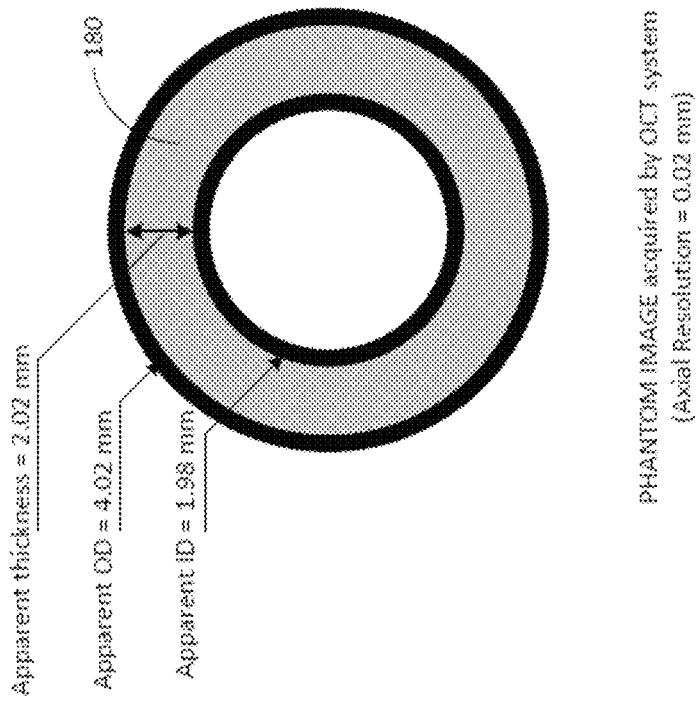
FIG. 4C and FIG. 4D illustrate an example of how a measurement of the thickness of phantom 180 would be affected by blurriness related to axial resolution, according to an embodiment of the present disclosure.
Figure 4C:
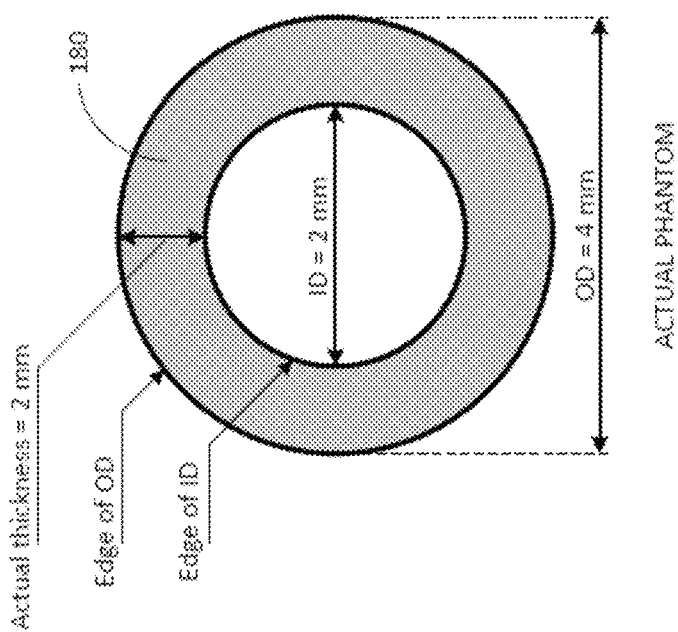

FIG. 4C and FIG. 4D illustrate an example of how a measurement of the phantom 180 would be affected by blurriness related to axial resolution. FIG. 4C shows an actual phantom 180 having an inner diameter of 2 mm, an outer diameter of 4 mm, and a wall thickness of 2 mm. FIG. 4D shows the blurring effects on an image of phantom 180 when acquiring an image of the phantom with an OCT system having an axial resolution of 20 microns (0.02 mm). In FIG. 4D, since each point along the edge of the ID and OD of the actual phantom 180 gets imaged as a 20 micron point, the image of phantom 180 shown on FIG. 4D has an apparent ID=1.98 mm, an apparent OD=4.02 mm, and an apparent thickness TH=2.02 mm. This causes an error of 20 microns on the perceived (measured) image of the phantom.

In present application, the z-offset can be accurately adjusted to match the measured ID of the phantom to the nominal value similar to a standard OCT z-offset calibration. However, using the phantom ID instead of the catheter's sheath OD avoids one or more errors of measurement due to unexpected changes in size and/or shape of the sheath. Therefore, it is advantageous that the catheter is calibrated for room temperature air before being inserted into the patient.

Once the catheter enters the body of a patient and acquires images through flushing media (angiographic contrast or saline solution), the system will need to be recalibrated but only for z-offset. The angle will change by the known ratio of indexes between the flush media and tissue, but this change in angle can be accounted for through the refractive index of media setting in the system. Therefore, z-offset calibration after the catheter enters the body of a patient can be done manually or automatically using known standard methods for calibrating to the sheath OD, but now rather than using the nominal OD of the catheter, the system can use the actual measured OD in the calibrated state and use that fiducial for ongoing calibration throughout procedure.

Figure 3B:
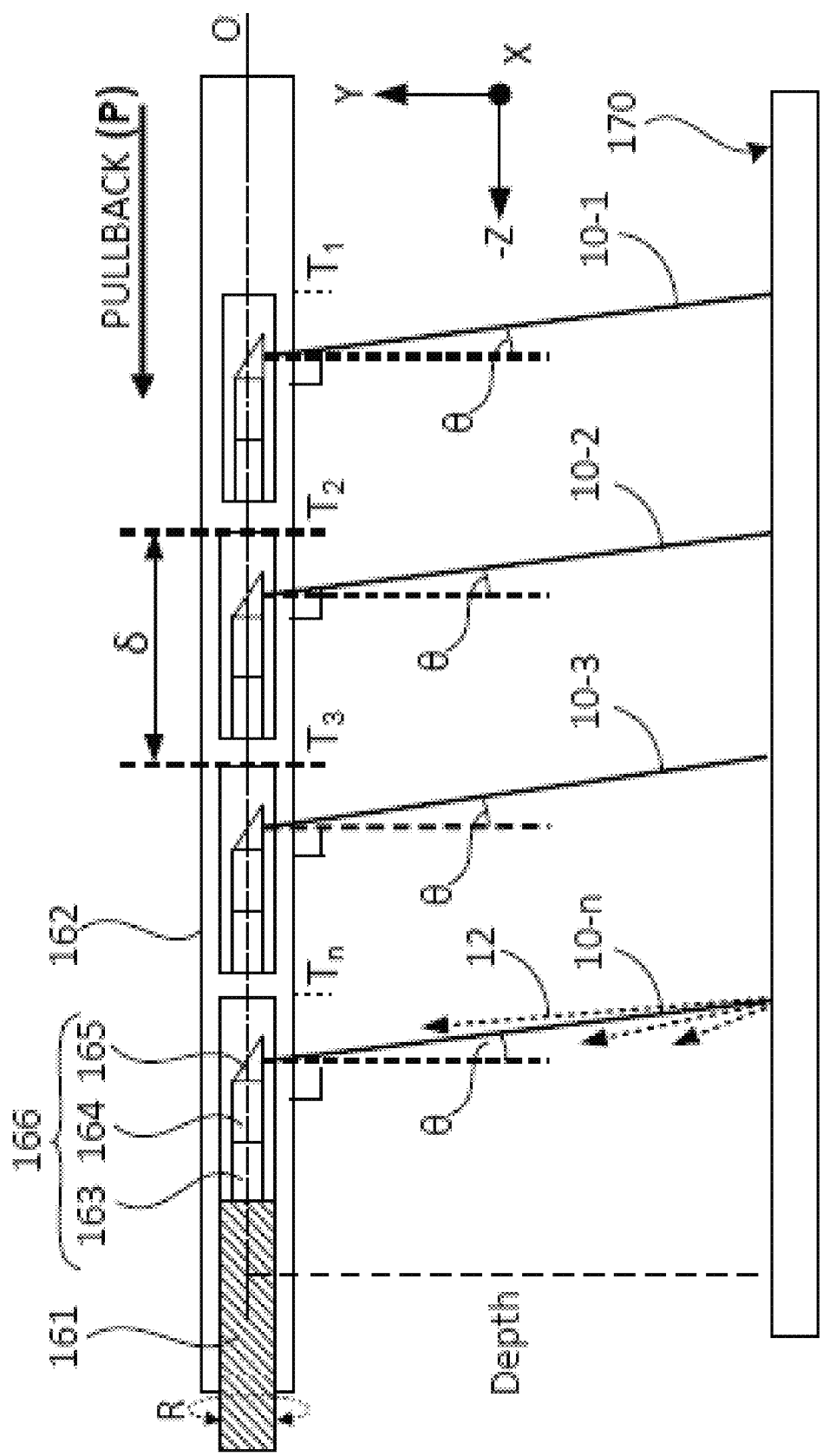
FIG. 3B illustrates an exemplary pullback operation where the catheter 160 scans a sample 170 at sequential positions to acquire an image of sample 170, such as a vessel, according to an embodiment of the present disclosure.

Referring back to FIG. 3B, an exemplary pullback operation where the catheter 160 scans a biological lumen 170 at sequential positions to acquire an image of the biological lumen 170, such as a vessel, is illustrated. As shown in FIG. 3B, the imaging core 190 is configured for side-view imaging, where a light beam 10 is emitted from the distal end of the catheter 160 at an angle theta ($\theta$) with respect to the catheter body. The light beam 10 is incident on the biological lumen 170 as the catheter is moved in a direction parallel to the catheter axis Ox. Here, as the light beam 10 irradiates a biological lumen (e.g., a vessel wall), the imaging core rotates or oscillates (as indicated by arrow R) about the catheter axis Ox, and is pulled back (in direction P) inside the sheath 162 which remains stationary. The distal optics assembly 166 collects backscattered light 12 from the plurality of locations along the length of biological lumen 170 while the imaging core 190 continuously rotates and travels back in direction P. In this manner, the catheter 160 can continuously scan the biological lumen 170 with the light beam 10 in a helical fashion through successive rotations. The combination of backscattered light from the light beam 10 and reference light from the reference beam (not shown) results in a pattern of the interference signals, only when light from both the sample and reference arms have traveled substantially the same optical distance (where "substantially the same optical distance" indicates a difference of less than or equal to the coherence length of the light source). Regions of the biological lumen that reflect more light will create stronger interference signals than regions that reflect less light. Any light that is outside the coherence length will not contribute to the interference signal. The intensity profile of the reflected light, which is referred to as an A-scan or an A-line scan, contains information about the spatial dimensions and depth location of structures within the biological lumen.

Once the z-offset and beam angle are determined at room temperature calibration, the catheter is accurate for all measurements. For simplicity and for the purpose of this disclosure, the biological lumen 170 can be thought of as a substantially cylindrical lumen. But as mentioned earlier, the optical length of the catheter can change during in vivo use of the catheter inside bodily lumens. The optical path length can change due to temperature increase when first inserted in a body and it can change slightly from moment to moment based on stretching from bending or from forces during rotation and translation. That's where a need for continuous calibration arises. In the present disclosure, the initial z-offset calibration obtained by using the calibration phantom prior to an intraluminal intervention is used to expose internal catheter reflections for automated continuous calibration during an intervention, as described with reference to FIG. 7.

<Distal Optics Signature for OCT Image Calibration>

In order to automate ongoing calibration after the catheter is removed from the phantom and inserted into a biological lumen, the system needs to target a new calibration fiducial in the catheter itself which will remain present in vivo. In the present disclosure, the sheath OD can be used similar to the conventional method described by Friedman. However, a more accurate calibration can be achieved by using the initial phantom calibration to improve the conventional calibration fiducial. According to the present disclosure, improved ongoing calibration is achieved using the catheter sheath, by measuring the OD of the sheath while the catheter is in the phantom after initial calibration. In this case, the measured OD of the sheath is stored in the system, and then the sheath is adjusted to that value on subsequent images instead of using the nominal sheath diameter. This process removes calibration errors due to the sheath diameter variability.

An even more accurate continuous calibration can be achieved by using other reflective surfaces within the distal optics of the imaging probe in the catheter. In this case, instead of using pre-selected surfaces with known real diameters, the system can be configured to effectively capture a snapshot of all the surfaces and signals within the lens as they actually appear while the catheter is calibrated with the phantom. Then, during intraluminal imaging in-vivo, the system is configured to match the pattern acquired during initial calibration to maintain continuous calibration for each A-line scan and/or each B-scan (frame) of the OCT image.

Figure 5:
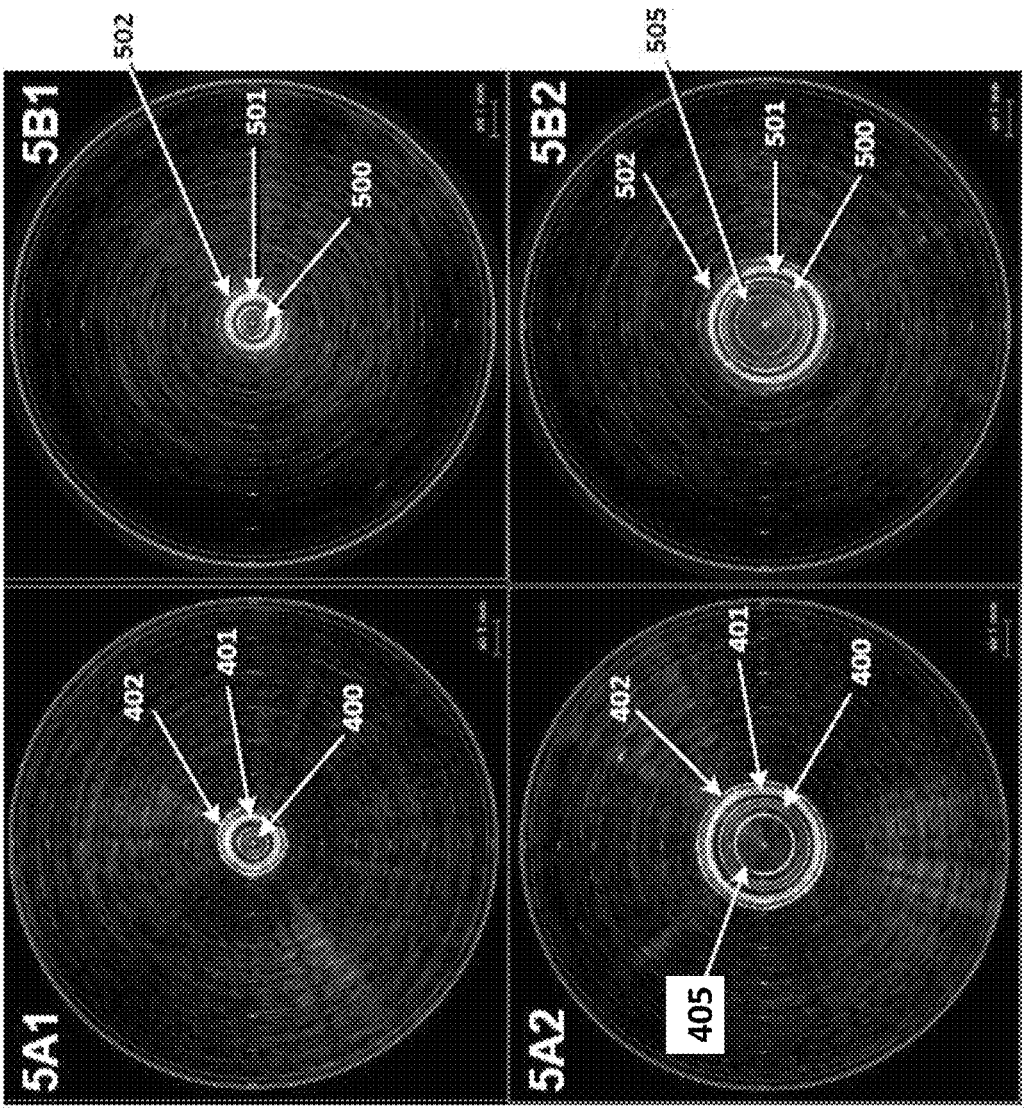
FIG. 5 shows a series of OCT images to illustrate the concept of continuous calibration using a signal acquired during initial calibration with the calibration phantom, according to an embodiment of the present disclosure.

FIG. 5 shows a series of OCT images to illustrate the concept of z-offset calibration using a feature or pattern of features acquired during initial calibration with the phantom. According to one embodiment, after achieving initial calibration in the phantom 180, the reference arm can be shifted by a fixed amount such as, for example, 0.5 mm which expands the sheath (moves the sheath line) on the OCT image. This can expose additional rings/reflections from further surfaces proximally within the lens and/or optical fiber endface which would otherwise be filtered out of the image. The system can use those additional rings/reflections of the catheter acquired during initial calibration as stand-in fiducials. Imaging is performed with the z-offset shifted where calibration uses the internal rings/reflections as fiducials, and final image display shifts back the image to proper calibrated state where those internal fiducials are no longer present.

In FIG. 5, an image 5A1 shows an OCT image acquired by a first catheter, and image 5B1 shows an OCT image acquired by a second catheter different from the first catheter. The first catheter may have acquired image 5A1 under room temperature air, while the second catheter may have acquired image 5B1 under flushing media. Both OCT images are calibrated in a known conventional manner. In image 5A1, the inner most circle or ring represents intensity of light reflected from the outside surface of the lens (lens surface reflection 400); the middle circle or ring represents intensity of light reflected from the catheter sheath (sheath reflection 401); and the outermost circle or ring represents intensity of ghost reflections from the sheath (ghost reflection 402). Similarly, in image 5B1, the inner most circle or ring represents intensity of light reflected from the outside surface of the lens (lens surface reflection 500); the middle circle or ring represents intensity of light reflected from the catheter sheath (catheter reflection 501); and the outermost circle or ring represents intensity of ghost reflections from the sheath (ghost reflection 502).

Conventionally, the surface most commonly used for z-offset calibration is the signal corresponding to reflections from the catheter sheath (i.e., sheath reflection 401 or sheath reflection 501). However, the ghost reflections from the sheath make it harder to accurately calibrate to the sheath surface. Moreover, depending on the media in which the catheter is in, the sheath image can vary in appearance and/or size. For example, in image 5B1, the sheath reflections 501 and ghost reflections 502 are more blurred than the corresponding signals in image 5A1. This situation can make the calibration process suboptimal because the sheath surface is not accurately defined for calibration. Therefore, prior publications such as described by Kemp (U.S. patent Ser. No. 10/206,585) or Petersen (U.S. Pat. No. 8,116,605) have proposed to calibrate the catheter to surfaces other than the sheath, as an alternate calibration surface for more precision. However, in these prior publications, the calibration surfaces are integrated in the catheter itself, and therefore can still be subject to errors.

According to the present disclosure, after achieving initial calibration at room temperature in the phantom, the reference arm can be shifted by a fixed amount such as 0.5 mm which expands (moves) the sheath on the OCT image. This can expose additional features such as rings/surfaces from further proximally within the distal optics (lens/optical fiber) which would otherwise be filtered out of the image. Then, the system can use these additional features to perform ongoing calibration.

In FIG. 5, image 5A2 illustrates a first OCT image acquired by the first catheter after the reference arm is shifted by a predetermined amount (e.g., 0.05 mm). Image 5B2 illustrates a second OCT image acquired by the second catheter also after the reference arm is shifted by 0.5 mm. Image 5A2 is an OCT image with z-offset shifted by 0.5 mm to show a new surface represented by a new inner most ring 405. As it is shown, image 5A2 is an incorrectly calibrated image now that a new surface reflection has appeared. This surface was at or inside the origin and not visible in the previously calibrated image 5A1. If imaging is performed with this z-offset shift in place then the inner most ring 405 can be used as a new alternate calibration surface. In the end, after completing imaging, the images can be shifted back to the origin, and this surface will disappear.

Image 5B2 shows the same process as in image 5A2 in a different catheter to show the variation in appearance due to the media in which the catheter is in. The exterior sheath surface appears more blurry here and would be more difficult to calibrate to the sheath surface. However, in this case, the position and amplitude of the internal reflection 505 (corresponding to one or more reflective surfaces of the imaging optics) provide a stable signature for the catheter. That is, the internal reflection ring 505 is a stable (unchanging) signature independent of the flushing media through which the OCT image is acquired.

Therefore, in at least one embodiment, the system can be trained to recognize the specific pattern of a given catheter in this expanded calibration state. Then subsequent imaging can be performed in this expanded state with the pattern used to maintain the expanded calibration through temperature and media changes. Once all image frames are individually calibrated, the image can be shifted back inward in polar coordinates to remove the 0.5 mm shift/expansion, and restore the correct calibration while maintaining the accuracy of the initial phantom calibration. In other words, the system can adjust the reference to visualize optical reflection signals, acquire data like that, then use the visualized signals for calibration on each frame and then, importantly, reverse the shift to restore the image to the properly calibrated state.

<Calibration Algorithms>

Figure 6:
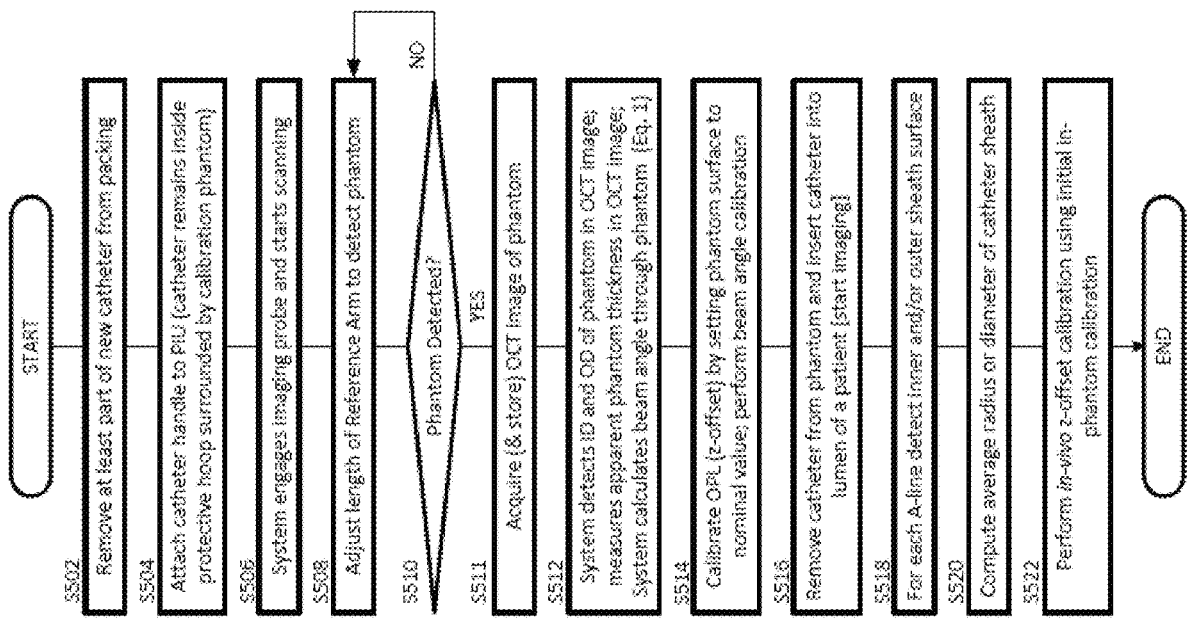
FIG. 6 shows an example calibration algorithm for one time calibration with manual correction, according to an embodiment of the present disclosure.

According to one embodiment, initial calibration is done according to the flowchart shown in FIG. 6 only to achieve calibration at room temperature in air using the calibration phantom 180. After initial calibration at room temperature, re-calibration in the patient's body can be achieved by any standard z-offset calibration method, e.g., by using the sheath OD to calibrate to the nominal catheter OD. This solution will provide a more accurate result than with conventional standard calibration due to the reduction in angle error and the use of a stable reference signature provided by the calibration phantom.

According to the flowchart of FIG. 6, one time calibration with manual correction starts at step S502. At step S502, the user removes at least part of the new catheter 160 (e.g., the handle 150) from the outer packaging (e.g., the user removes at least part of the die card, plastic box, shrink wrap, etc. to expose at least the handle 150). At step S504, the user attaches the catheter connector 151 to the PIU 120 while maintaining the catheter 160 (probing portion) still in the protective hoop 181. At step S504, the system detects attachment of the catheter handle. At step S506, upon detecting catheter attachment to the PIU, the system automatically initiates an optical connection routine to engage the imaging probe to the pullback unit, and starts imaging. At step S508, the system adjusts the optical path length (OPL) of the reference arm so that the lens of the imaging probe is aligned with the phantom 180. At step S508, the system may be programmed to iteratively adjust the OPL of the reference arm until the phantom 180 is identified from an image or from a backscattered signal detected by the system. As mentioned above, the phantom 180 can be made of polymer containing doped particles such as TiO2 to enhance backscattering of light having a wavelength or a range of wavelengths specific to OCT imaging.

As mentioned above, to adjust the OPL of the reference arm, the system can be equipped with an optical delay line. In an embodiment, the optical delay line may include a mirror placed on a linearly scanning galvanometer in the reference arm. In other embodiments, the optical delay line can be a fixed-length reference fiber coil (e.g., a segment of optical fiber) that is placed in the reference arm to match the reference arm's optical path length to the sample arm's optical path length.

At step S510, the system determines if the phantom has been detected in the OCT image and/or backscattered signal. If the phantom is not detected in the OCT image (NO at S510), the system continues to control movement of the MDL until the phantom is detected. In this instance, the system may prompt the user to move the phantom 180 so that it is within an imaging range of the imaging core 190. When the phantom is detected (YES at S510), the system stores an image of the phantom at step S511. Thereafter, the process advances to step S512. At step S512, the system detects the inner diameter and the outer diameter of the phantom in the OCT image. The system also determines (calculates) the phantom wall thickness in the OCT image based on the ID and/or the OD detected from the OCT image. Then, the system adjusts the beam angle to calibrate. Here it must be noted that we are not adjusting the wall thickness to the beam angle; we are calculating the actual beam angle from the measured wall thickness in the OCT image. All subsequent measurements use the newly determined actual beam angle instead of the pre-programmed nominal beam angle. As mentioned above, the manufactured thickness and index of refraction of the phantom 180 can be stored in the system memory. However, to accurately measure (calculate) the phantom wall thickness (TH) in the OCT image, the system can factor the beam angle by using Equation (1) combined with a difference between the mean OD and mean ID obtained from an actual image of the phantom (as shown in FIG. 4A and FIG. 4B).

At step S514, the system adjusts the z-offset by setting the phantom ID in the OCT image to the known nominal value. That is, the z-offset is adjusted to match the measured ID of the phantom in the image to the known nominal value like a standard OCT z-offset calibration but using the phantom ID instead of the sheath OD. At this point, the catheter is correctly calibrated under room temperature conditions. Here, the "known nominal value" is the known value of the phantom ID. The phantom is a manufactured object which will have a well-controlled and known ID and OD, and known index of refraction. Once the system measures the ID and OD in the image of the phantom, and calculates the phantom thickness in the OCT (all using the nominal beam angle), the system then calculates the actual beam angle based on the difference between the measured/calculated thickness and the known actual thickness of the phantom. With a new beam angle setting, the whole image will be scaled differently but now we know we have an accurate beam angle. From here, the system is setting the phantom ID to its correct dimension like a standard z-offset.

At step S516, the user removes the catheter from the protective hoop 181, and inserts the sterile catheter 160 into a biological lumen of a patient. This step S516 can be performed in a conventional manner. However, at the end room temperature calibration, the system will record the calibrated parameters in the system's memory, and can prompt the user to remove the calibration phantom prior to using the catheter in a patient.

At step S518, the system detects a signature feature (peak signal) corresponding to the OD of the catheter sheath for each A-line scan. At step S520, the system computes an average radius of the detected sheath. At step S522, since the catheter has entered the patient's body and acquires images through flush media (angiographic contrast or saline), the system will recalibrate only for z-offset.

Re-calibration inside the body can be achieved by the standard method of using the catheter OD to calibrate to the nominal OD. Since recalibration at body temperature is done after calibration at room temperature with the phantom, the recalibration will give a more accurate result than with standard calibration due to the reduction in angle error.

<Automated Continuous OCT Image Calibration>

In one embodiment, after initial calibration is done according to steps S502-S510 of FIG. 6, the system is trained to key-in on signals from the lens for subsequent calibration to achieve fully automated continuous calibration with no user input. A flowchart of the process for automated continuous calibration is illustrated in FIG. 7.

Figure 7:
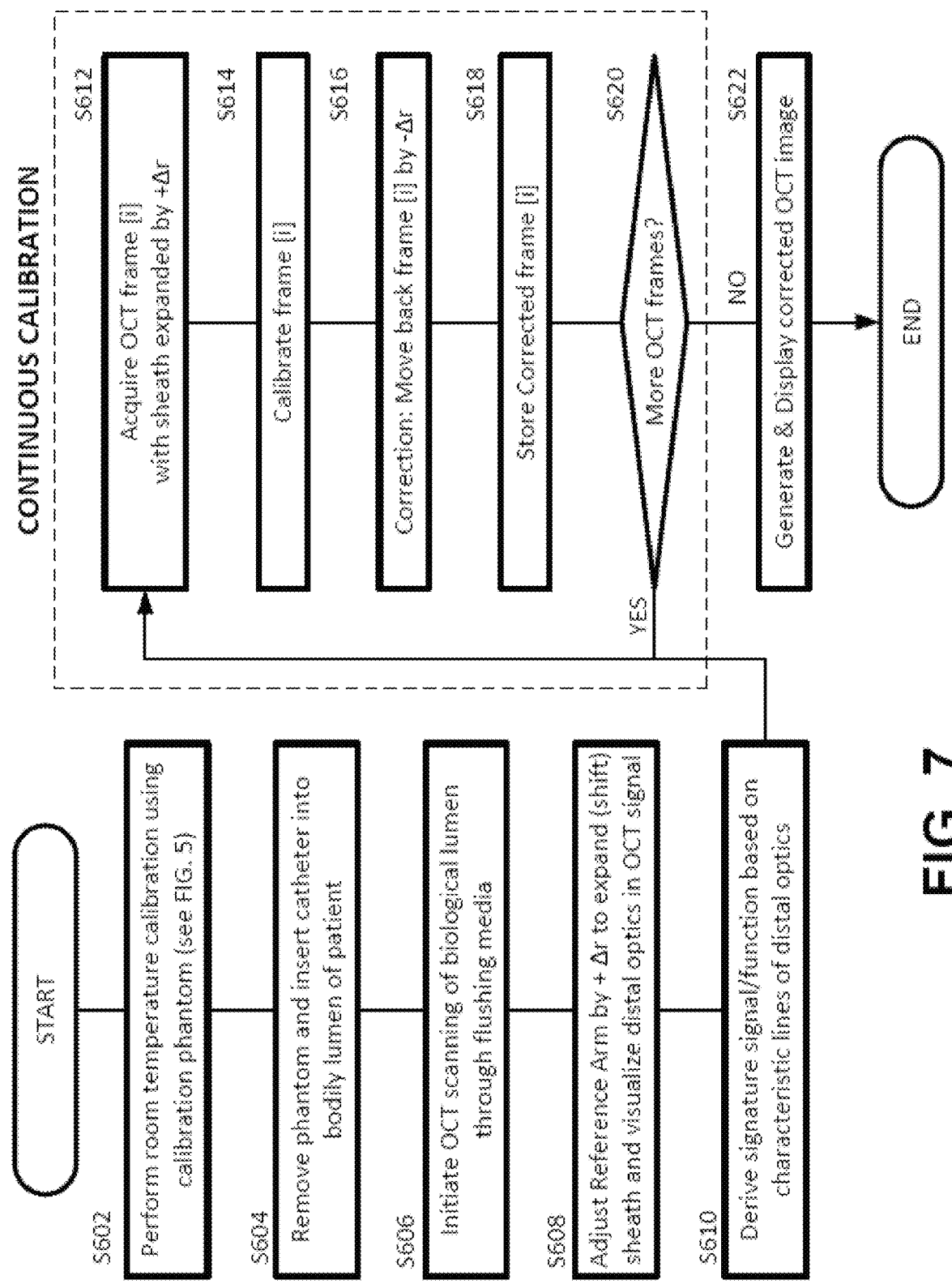
FIG. 7 shows an example calibration algorithm for automated continuous calibration, according to an embodiment of the present disclosure.

In FIG. 7, step S602 corresponds to the process of step S502 through S514 for room temperature calibration using the calibration phantom 180. At step S604, the user removes the phantom 180, and inserts the catheter 160 into a bodily lumen of a patient. When the distal tip of the catheter is at a desired location, flushing and pullback are triggered in a known manner. At step S606, the system acquires an initial OCT image through flush media (image contrast or saline solution). At step S608, the system adjusts the reference arm to shift (expand) the sheath by a predetermined distance (Δr). In an embodiment, the sheath is expanded (shifted) by a distance sufficient to visualize one or more characteristic lines corresponding to reflections from the distal optics (e.g., a line corresponding to light reflected by the fiber endface, of by the lens surfaces, and/or by the beam directing surface). At step S610, the system derives a signature function based on characteristic of the one or more lines of the distal optics. A signature function may be derived by detecting amplitude peaks, thicknesses, and/or separation of lines from the detected signals, and averaging the most prominent or desired signals that can be used for calibration.

At steps S612-S620, the system performs in vivo OCT imaging of the lumen sample during a pullback operation with continuous calibration. More specifically, at step S612, the system starts to acquire an OCT image with the sheath expanded by the predetermined distance (+Δr). At step S614, the system performs z-offset calibration on each A-line and/or each frame (B-frame) of the OCT image. Here, z-offset calibration would be done on each frame by looking at the signature reference circles in the lens and adjusting the z-offset if necessary on that frame to put those circles at their predetermined positions matching where they were when the catheter was in the phantom. To that end, circles as those shown in FIG. 5 can be used.

At step S616, the system moves each A-line or each frame of the OCT image back to the center of the image by reducing/shifting the sheath by an amount equal to the predetermined distance but in the opposite direction (−Δr). At step S618, the system stores each correctly calibrated A-line or correctly calibrated B-frame in the system's memory. At step S620, the system determines if continuous calibration is complete (e.g., if all frames are calibrated). The process of steps S612 though S620 is repeated until all OCT frames are correctly calibrated and processed. At step S622, the system outputs the corrected OCT image to the screen of display 300.

Figure 8:
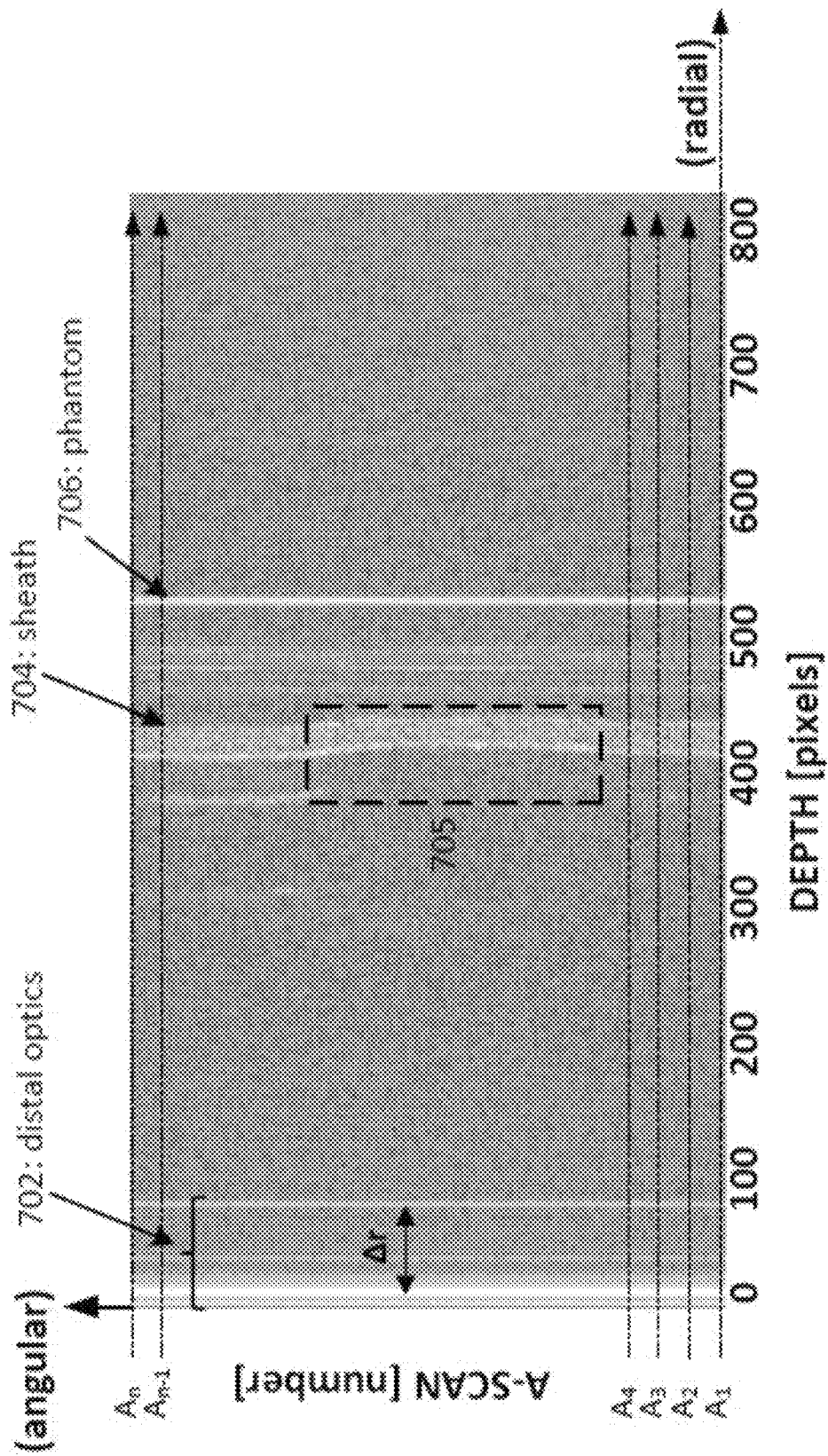
FIG. 8 illustrates an exemplary OCT B-scan frame in polar coordinates where the OCT signal is shifted by an amount Or of radius to more accurately perform z-offset calibration, according to an embodiment of the present disclosure.

FIG. 8 illustrates an example of an OCT B-scan frame in polar coordinates where the OCT signal is shifted by an amount +Δr of radius. The horizontal axis represents the radial distance from the center of the catheter, and the vertical axis represents the angular direction from 0 to $2\pi$ radians (0 to 360 degrees). In FIG. 8, a signature feature or signature signal 702 corresponds to reflections from one or more surfaces of the distal optics assembly 166 (fiber endface, lens, or beam directing component), a sheath signal 704 corresponds to reflections from the outer catheter sheath 162 (e.g. the inner diameter of the outer sheath), and a phantom signal 706 corresponds to light reflected or backscattered from the calibration phantom 180. For example the phantom signal 706 corresponds to the inner surface of the calibration phantom 180. An OCT image of the type shown in FIG. 8 can be acquired and recorded during the initial calibration (at room temperature air), and used later as reference during in-body continuous calibration.

In FIG. 8, the sheath signal 704 shows a region 705 where the lines corresponding to the sheath surface has a variation in diameter due to, for example, NURD or sheath non-concentricity. In contrast, the phantom signal 706 is substantially straight and parallel to the vertical axis, so that the signal corresponding to calibration phantom (phantom signal 706) can be easily distinguishable in the OCT frame on a line-by-line basis. Therefore, accurate calibration can also be done using OCT images in polar coordinates where an OCT image with the sheath expanded by the predetermined distance (+Δr) can be processed on a frame-by-frame basis (or A-line by A-line basis). And after processing each frame (or line) of the image for calibration, the system moves each frame (or line) of the OCT image back towards the center of the image by reducing/shifting the sheath signal 704 by an amount equal to the predetermined distance but in the opposite direction (−Δr). In this manner, after calibrating in phantom, the system can perform a z-offset shift to expose internal catheter reflections which would otherwise be outside the field of view, and use those internal catheter reflections as the stand-in fiducials. Imaging is performed with the z-offset shifted, calibration uses the internal catheter reflections as fiducials, and final image display shifts back to the proper calibrated state where those internal catheter reflections are no longer shown.

<Additional Calibration Factors>

Additional embodiments can add additional features to the phantom calibration process to achieve further optimizations including, but not limited to:

One or more phantoms with controlled doping concentration or polymers with homogeneous OCT appearance can be used to adjust display settings or system output power gain to account for variations in collection efficiency or transmission of light through the catheter, and produce an image with calibrated brightness or optimized signal to noise ratios. Catheters can vary in brightness based on collection efficiency. If the phantom has a precisely controlled concentration of TiO2 doping, the phantom would be expected to always appear with the same brightness on an OCT image (same average signal intensity for all pixels in the phantom image) if the catheters had equivalent efficiency. But a catheter with low collection efficiency will give a dimmer appearing image. The system display brightness could be adjusted during the phantom calibration step to make the apparent brightness of the phantom image consistent; this will yield more consistent image appearance during in vivo imaging.

One or more phantoms with other additives such as fluorophores or materials with specific spectrographic content can be used to calibrate a second imaging modality for a dual modality or multimodality imaging system that co-registers OCT imaging with functional modalities like near infrared fluorescence (NIRF), near infrared auto fluorescence (NIRAF), or spectroscopy (e.g., confocal spectroscopy).

One or more phantoms with a regularly repeating pattern in the ID or OD, where the pattern is designed to be is visible and particularly distinguishable in OCT images, can be used to detect distortions from NURD or vibrations or other artifacts as a quality check to screen out devices that are not functioning adequately out of the sterile packaging prior to using such devices in a patient. For example, multimodality OCT (MMOCT) uses a first optical channel to detect OCT signals and a second optical channel to detect fluorescence signals from tissue. In a MMOCT system, the catheter is very sensitive and linear at detecting changes in NIRAF but not very accurate in quantifying actual underlying NIRAF intensity due to variable collection efficiency. In this case, for example, the system can be equipped with two phantoms including a first phantom having a certain level or type of doping to be imaged under OCT and a second phantom having a different level or type of doping to produce twice the fluorescent intensity of the first. If the two phantoms are imaged with 2 different catheters, the system would consistently see one as twice as bright in the image as the other but the raw values between the 2 catheters could vary by around +/−25%. Using a phantom with a precise, controlled amount of fluorescence would allow the system to adjust gain such that every catheter was giving the same raw value for NIRAF in the phantom, which would make all NIRAF measurements much more accurate and repeatable.

In summary, in order to provide a more accurate calibration technique, the present application proposes a phantom with specified optical properties which can be used to provide additional calibration fiducials which span the imaging range of the system. In one embodiment, a circular phantom with accurate ID and OD and known index of refraction is built into the catheter packaging and is imaged by the catheter upon first connection to the OCT system without removing the catheter from the packaging. In other embodiments, the phantom can be provided separately (e.g., permanently fixed to the system). Instead of calibrating with one degree of freedom (z-offset) to one fiducial (the sheath OD) as is conventional practice, the system disclosed herein can calibrate with two degrees of freedom (z-offset and beam angle) by using two fiducials (ID and OD of phantom). This novel technique can minimize the risks of measurement error, can make calibration easier to automate continuous calibration, can reduce one or more sources of calibration error, and can particularly reduce the beam angle error resulting in an improvement in accuracy at all diameters of the most commonly used catheters.

<Software Related Disclosure>

At least certain aspects of the exemplary embodiments described herein can be realized by a computer of a system or apparatus that reads out and executes computer executable instructions (e.g., one or more programs or executable code) recorded on a storage medium (which may also be referred to as a 'non-transitory computer-readable storage medium') to perform functions of one or more block diagrams or flowchart diagrams described above. For example, at least part of the processes or functions represented by FIG. 6, FIG. 7 and FIG. 8 can be implemented by computer 200.

The computer may include various components known to a person having ordinary skill in the art. For example, the computer may include signal processor implemented by one or more circuits (e.g., a field programmable gate array (FPGA) or an application specific integrated circuit (ASIC)) for performing the functions of one or more of the above-described embodiment(s), by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)), and may include a network of separate computers or separate processors to read out and execute the computer executable instructions. The computer executable instructions may be provided to the computer, for example, from a cloud-based network or from the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. The computer may include an input/output (I/O) interface to receive and/or send communication signals (data) to input and output devices, which may include a keyboard, a display, a mouse, a touch screen, touchless interface (e.g., a gesture recognition device) a printing device, a light pen, an optical storage device, a scanner, a microphone, a camera, a drive, communication cable and a network (either wired or wireless).

The foregoing embodiments provide a number of advantages over known standard z-offset calibration techniques. Whereas conventional calibration techniques rely on a built-in fiducial surface with one diameter or a built-in reflector with two surfaces to adjust z-offset to account for variation in optical path length, the inventor of the present application recognizes that OCT catheters also vary in beam angle, which is not conventionally addressed. It should be noted that the z-offset calibration method of present application does not rely on special doped catheter sheath design, nor does it rely on fixed structures of the catheter.

According to an embodiment of the present disclosure, an OCT system uses a calibration phantom with two surfaces covering a distance at least equal to the full field of view of the system to improve basic calibration for optical path length. Notably, the calibration phantom is not part of the catheter, and the two surfaces are used as stable fiducials which are not affected by variations in catheter length or catheter angle. According to an embodiment of the present disclosure, the OCT system uses a phantom with two or more fiducials with known distance between them (thickness) to account for both variation in optical length and variation in beam angle. This new type of OCT calibration provides an extra degree of freedom to achieve better calibration accuracy.

According to a further embodiment of the present disclosure, after calibrating in phantom, the system can identify a new fiducial on catheter (can be the sheath OD which is commonly used for calibration but now rather than using the nominal OD of the catheter the system can use the actual measured OD in the calibrated state) and use that fiducial as stand-in for the phantom in ongoing calibration throughout a procedure. According to a further embodiment of the present disclosure, after calibrating in phantom, the system can perform a z-offset shift to expose internal catheter reflections which would otherwise be outside the field of view and use those internal catheter reflections as the stand-in fiducials for the phantom. Imaging is performed with the z-offset shifted, then calibration uses the internal fiducials, and final image display shifts back to the proper calibrated state where those internal fiducials are no longer present.

According to an embodiment, the present disclosure provides a novel z-offset calibration for existing OCT systems (i.e., the calibration phantom can be implemented without significant modification to commercially available OCT systems). Provides scaling calibration for an OCT system. The phantom can be built into catheter packaging or integrated into a protective hoop for ease of use and safety. In some embodiments, the phantom can be provided as a component separate from the catheter packaging. In such embodiments, the phantom can be installed or attached to the system console or to the patient interface unit (PIU). Among the various embodiments, at least one embodiment provides a non-variable reference for automated continuous calibration for in vivo imaging; the calibration phantom avoids calibration errors by eliminating variation in size and/or shape of the catheter sheath. At least one embodiment avoids or at least minimizes calibration errors due to distortions of the sheath by controlling for NURD. At least one embodiment provides means for continuous calibration across pullbacks. At least one embodiment accounts for variation in catheter length to produce accurate measurements especially for small vessel diameters. At least one embodiment accounts for variation in catheter beam angle to produce accurate measurements especially for catheters of large diameters. According to at least one embodiment, z-offset calibration can be performed automatically on connection without even removing the catheter from its sterile packaging. According to at least one embodiment, z-offset calibration can be done by the system upon connection with or without user input. According to at least one embodiment, because the system can use an unchanging feature for continuous calibration, the system maintains calibration accuracy throughout a procedure regardless of changes in temperature and/or flushing media.

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by persons of ordinary skill in the art to which this disclosure belongs. In that regard, breadth and scope of the present disclosure is not limited by the specification or drawings, but rather only by the plain meaning of the claim terms employed.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner. To that end, the scope of the following claims is to be accorded the broadest interpretation so as to encompass all such modifications and equivalent structures and functions.

Any patent, pre-grant patent publication, or other disclosure, in whole or in part, that is said to be incorporated by reference herein is incorporated only to the extent that the incorporated materials do not conflict with standard definitions or terms, or with statements and descriptions set forth in the present disclosure. As such, and to the extent necessary, the disclosure as explicitly set forth herein supersedes any conflicting material incorporated by reference.

What is claimed is:

1. A method of calibrating an optical coherence tomography (OCT) system, the OCT system comprising a catheter having a catheter sheath spanning from a proximal end to a distal end, wherein the catheter includes an imaging core enclosed inside the catheter sheath and configured to guide a light beam from the distal end of the catheter sheath at a nominal angle with respect to the catheter sheath, the method comprising:
controlling the imaging core to scan a cylindrical phantom which has a known thickness;
acquiring an OCT image of the cylindrical phantom by transmitting the light beam through the cylindrical phantom, and collecting light reflected and/or backscattered from an inner surface and an outer surface of the cylindrical phantom;
displaying the OCT image of the cylindrical phantom on a display device;
determining a location of the inner surface and a location of the outer surface of the cylindrical phantom within the OCT image; and
setting the location of the inner surface and/or the location of the outer surface of the cylindrical phantom within the OCT image to an initial z-offset position to correct for variations in optical path length of the catheter.

2. The method according to claim 1, further comprising:
measuring a thickness of the cylindrical phantom shown in the OCT image based on the location of the inner surface and the location of the outer surface of the cylindrical phantom within the OCT image,
wherein setting the location of the inner surface and/or the location of the outer surface of the cylindrical phantom to the initial z-offset position is based on a difference between the measured thickness of the cylindrical phantom in the OCT image and the known thickness of the cylindrical phantom.

3. The method according to claim 1, further comprising:
calculating an angle of the light beam transmitted through the cylindrical phantom based on a distance traveled by the light beam from the inner surface to the outer surface of the cylindrical phantom,
wherein setting the location of the inner surface and/or the location of the outer surface of the cylindrical phantom to the initial z-offset position is based on a difference between the calculated angle of the light beam and the nominal angle of the light beam.

4. The method according to claim 1, further comprising:
identifying, within the OCT image of the cylindrical phantom, at least one line corresponding to internal catheter reflections; and
using the at least one line corresponding to the internal catheter reflections as a fiducial for ongoing calibration throughout an intraluminal procedure.

5. The method according to claim 1, further comprising:
shifting the initial z-offset position by a predetermined distance sufficient to visualize one or more lines corresponding to optical reflections from distal optics included in the imaging core;
acquiring an OCT image of a biological lumen while the initial z-offset position remains shifted by the predetermined distance;
calibrating the OCT image of the biological lumen to the one or more lines corresponding to the optical reflections from distal optics;
shifting back the calibrated OCT image of the biological lumen to the initial z-offset position; and
displaying the OCT image of the biological lumen without the one or more lines corresponding to optical reflections from distal optics.

6. The method according to claim 1, further comprising:
shifting the initial z-offset position by a predetermined distance sufficient to visualize one or more lines corresponding to optical reflections from the catheter sheath;
inserting the catheter sheath into a biological lumen of a patient without the calibration phantom; and
controlling the imaging core to acquire an OCT image of the biological lumen of the patient while the initial z-offset position remains shifted by the predetermined distance,
wherein the OCT image of the biological lumen includes a plurality of image frames acquired during a pullback operation of the imaging core.

7. The method according to claim 6, further comprising:
calibrating the OCT image of the biological lumen to the one or more lines corresponding to the optical reflections from catheter sheath;
shifting back the calibrated OCT image of the biological lumen to the initial z-offset position; and
displaying the OCT image of the biological lumen calibrated to the initial z-offset position.

8. The method according to claim 1,
wherein determining the location of the inner surface of the cylindrical phantom within the OCT image includes calculating a mean inner diameter (ID) of the cylindrical phantom based on an averaged OCT signal reflected and/or backscattered from the inner surface, and determining the location of the outer surface of the cylindrical phantom in the OCT image includes calculating a mean outer diameter (OD) of the cylindrical phantom based on an averaged OCT signal reflected and/or backscattered from the outer surface.

9. The method according to claim 6, further comprising:
calculating a thickness of the cylindrical phantom in the OCT image,
wherein the thickness of the cylindrical phantom in the OCT image is the mathematical difference of the mean OD minus the mean ID.

10. The method according to claim 7, further comprising:
calculating the angle of the light beam transmitted through the cylindrical phantom based on the following formula Eq. (1):

$$\theta_{cath} = \arccos(L_{nom} * \cos(\theta_{nom})/(L_m - R_A)) \quad \text{Eq. (1)}$$

where:
$\theta_{cath}$ is the angle of the light beam transmitted through the calibration phantom,
$\theta_{nom}$ is the nominal angle of the light beam emitted by the imaging core,
$L_{nom}$ is the known thickness of the calibration phantom,
$R_A$ is an axial resolution of the OCT system, and
$L_m$ is the calculated thickness of the calibration phantom in the OCT image.

11. An optical coherence tomographic (OCT) imaging system, comprising:
a catheter having a catheter sheath spanning from a proximal end to a distal end along a catheter axis;
an imaging core enclosed inside the catheter sheath and configured to guide a light beam from the distal end of the catheter sheath at a nominal angle with respect to the catheter sheath; and
a processor configured to:
control the imaging core to scan a cylindrical phantom which has a known thickness, wherein the imaging core acquires the OCT image of the cylindrical phantom by transmitting the light beam through the cylindrical phantom, and collecting light reflected and/or backscattered from an inner surface and an outer surface of the cylindrical phantom;
display the OCT image of the cylindrical phantom on a display device;
determine a location of the inner surface and a location of the outer surface of the cylindrical phantom within the OCT image; and
set the location of the inner surface and/or the location of the outer surface of the cylindrical phantom within the OCT image to an initial z-offset position to correct for variations in optical path length of the catheter and/or variations in the nominal of the light beam.

12. The system according to claim 11,
wherein the processor is further configured to measure an apparent thickness of the cylindrical phantom based on the location of the inner surface and the location of the outer surface of the cylindrical phantom within the OCT image, and
wherein the processor shifts the location of the inner surface and/or the location of the outer surface of the cylindrical phantom within the OCT image to the first z-offset position, based on a difference between the measured thickness of the cylindrical phantom in the OCT image and the nominal thickness of the cylindrical phantom.

13. The system according to claim 11,
wherein the processor is further configured to calculate an angle of the light beam transmitted through the calibration phantom based on a distance traveled by the light beam from the inner surface to the outer surface of the cylindrical phantom, and
wherein the processor sets the location of the inner surface and/or the location of the outer surface of the cylindrical phantom within the OCT image to the first z-offset position, based on a difference between the calculated angle of the light beam and the nominal angle of the light beam.

14. The system according to claim 11, wherein the processor is further configured to:

identify, within the OCT image of the cylindrical phantom, at least one line corresponding to internal catheter reflections; and
use the at least one line corresponding to the internal catheter reflections as a fiducial for ongoing calibration throughout an intraluminal procedure.

15. The system according to claim 11, wherein the processor is further configured to:
shift the initial z-offset position by a predetermined distance sufficient to visualize one or more lines corresponding to optical reflections from distal optics included in the imaging core;
acquire an OCT image of a biological lumen while the initial z-offset position remains shifted by the predetermined distance;
calibrate the OCT image of the biological lumen to the one or more lines corresponding to the optical reflections from distal optics;
shift back the calibrated OCT image of the biological lumen to the initial z-offset position; and
display the OCT image of the biological lumen in the display device without the one or more lines corresponding to optical reflections from distal optics.

16. The system according to claim 11, wherein the processor is further configured to:
wherein the processor determines the location of the inner surface of the cylindrical phantom within the OCT image by calculating a mean inner diameter (ID) of the cylindrical phantom based on an averaged OCT signal reflected and/or backscattered from the inner surface, and determines the location of the outer surface of the cylindrical phantom in the OCT image by calculating a mean outer diameter (OD) of the cylindrical phantom based on an averaged OCT signal reflected and/or backscattered from the outer surface.

17. The system according to claim 16, wherein the processor is further configured to:
calculate a thickness of the cylindrical phantom in the OCT image as the mathematical difference of the mean OD minus the mean ID.

18. The system according to claim 17,
wherein the processor calculates the angle of the light beam transmitted through the calibration phantom based on the following formula Eq. (1):

$$\theta_{cath} = \arccos(L_{nom} * \cos(\theta_{nom})/(L_m - R_A)) \quad \text{Eq. (1)}$$

where:
$\theta_{cath}$ is the angle of the light beam transmitted through the calibration phantom,
$\theta_{nom}$ is the nominal angle of the light beam emitted by the imaging core,
$L_{nom}$ is the known thickness of the calibration phantom,
$R_A$ is an axial resolution of the OCT system, and
$L_m$ is the calculated thickness of the calibration phantom in the OCT image.

19. The system according to claim 11, further comprising:
a protective hoop configured to hold the catheter in a sterile state,
wherein the cylindrical phantom is integrated within the protective hoop or attached to the protective hoop such that the cylindrical phantom intersects the light beam emitted from the catheter.

20. The system according to claim 11,
wherein the cylindrical phantom is made of glass or transparent polymer material doped or undoped with scattering agents to enhance visibility under OCT imaging, wherein the cylindrical phantom is either (a) built into a catheter packaging, (b) provided separate from the catheter packaging, or (c) permanently installed on/with the OCT system, and wherein the cylindrical phantom is imaged by the imaging core upon first connection of the catheter to the OCT system without removing the catheter from the catheter packaging.

21. The system according to claim 16, wherein the ID of the cylindrical phantom has a dimension substantially equal to an OD of the catheter sheath, and the OD of the cylindrical phantom is substantially equal to a maximum imaging range of the OCT system.

22. A method of using a calibration phantom for z-offset calibration of an optical coherence tomography (OCT) system, the OCT system comprising a reference arm and a sample arm having substantially equal optical paths lengths, the method comprising:

receiving a catheter enclosed within a sterile package, wherein the catheter includes a catheter handle and a catheter body spanning from a proximal end to a distal end with an imaging core enclosed inside the catheter body, and wherein the proximal end is configured to be connected to the OCT system via the catheter handle and the distal end is configured to guide a light beam at a nominal angle with respect to the catheter body;

removing at least the catheter handle from the sterile package;

attaching the catheter handle to the OCT system while the catheter body remains at least partially protected by the sterile packaging;

positioning the distal end of the catheter body inside a calibration phantom such that the calibration phantom is optically aligned with the light beam;

scanning the calibration phantom with the light beam;

forming an OCT image of the calibration phantom by collecting light reflected and/or backscattered from one or more surfaces of the calibration phantom;

detecting a positon of a first surface and/or a positon of a second surface of the calibration phantom within the OCT image; and performing z-offset calibration by the setting the position of the first surface and/or the position of the second surface of the calibration phantom in the OCT image to a nominal value, wherein the known nominal value is related to one or more of the known thickness of the calibration phantom or a diameter of the catheter body or the nominal angle of the light beam or a maximum imaging range of the OCT system.

* * * * *